United States Patent
Kehres et al.

(10) Patent No.: US 10,568,647 B2
(45) Date of Patent: Feb. 25, 2020

(54) PATIENT-SPECIFIC HUMERAL GUIDE DESIGNS

(71) Applicant: Biomet Manufacturing, LLC, Warsaw, IN (US)

(72) Inventors: Clinton E. Kehres, Warsaw, IN (US); Benjamin Isaiah Joseph, Grabill, IN (US); Nathan A. Winslow, Warsaw, IN (US); Jason M Hurst, New Albany, OH (US); Wolfgang Walter Vogt, Garmisch-Partenkirchen (DE)

(73) Assignee: Biomet Manufacturing, LLC, Warsaw, IN (US)

( * ) Notice: Subject to any disclaimer, the term of this patent is extended or adjusted under 35 U.S.C. 154(b) by 869 days.

(21) Appl. No.: 15/073,223

(22) Filed: Mar. 17, 2016

(65) Prior Publication Data

US 2016/0374697 A1     Dec. 29, 2016

Related U.S. Application Data

(63) Continuation-in-part of application No. 14/750,325, filed on Jun. 25, 2015, now Pat. No. 10,226,262.

(51) Int. Cl.
*A61B 17/17* (2006.01)
*A61B 17/15* (2006.01)
(Continued)

(52) U.S. Cl.
CPC .......... *A61B 17/1739* (2013.01); *A61B 17/15* (2013.01); *A61B 17/1778* (2016.11); *A61F 2/4612* (2013.01); *A61B 2017/568* (2013.01)

(58) Field of Classification Search
CPC . A61B 17/15; A61B 17/1555; A61B 17/1778; A61B 17/1739; A61B 2017/568;
(Continued)

(56) References Cited

U.S. PATENT DOCUMENTS

| 1,480,285 A | 1/1924 | Moore |
| 2,181,746 A | 11/1939 | Siebrandt |

(Continued)

FOREIGN PATENT DOCUMENTS

| CA | 2447694 A1 | 12/2002 |
| CA | 2501041 A1 | 4/2004 |

(Continued)

OTHER PUBLICATIONS

"U.S. Appl. No. 14 750,325, Final Office Action dated Aug. 8, 2018", 18 pgs.

(Continued)

*Primary Examiner* — Dinah Baria
(74) *Attorney, Agent, or Firm* — Schwegman Lundberg & Woessner, P.A.

(57) ABSTRACT

A humeral cut guide system for a humeral head comprises: a bone-engagement member including a first patient-specific bone-engagement surface that is complementary and made to substantially mate and nest in only one position on a specific patient's humeral head; a registration member connected to the bone-engagement member including a second patient-specific bone engagement surface that is sized and made to substantially mate and nest in only one position with the specific patient's bicipital groove; a first protrusion extending from the registration member and having a first surgeon-engaging surface for manipulation by a surgeon; and a cut guide plate connected to and extending away from the registration member such that, upon the bone-engagement member mating and nesting with the specific patient's humeral head, the cut guide plate is spaced apart from the humeral head, wherein the cut guide plate defines an elongate slot.

17 Claims, 14 Drawing Sheets

(51) Int. Cl.
*A61F 2/46* (2006.01)
*A61B 17/56* (2006.01)

(58) Field of Classification Search
CPC ... A61F 2/4612; A61F 2/40; A61F 2002/4011
See application file for complete search history.

(56) References Cited

U.S. PATENT DOCUMENTS

| | | |
|---|---|---|
| 2,407,845 A | 9/1946 | Orisan |
| 2,416,228 A | 2/1947 | Sheppard |
| 2,618,913 A | 11/1952 | Plancon et al. |
| 2,910,978 A | 11/1959 | Urist |
| 3,330,611 A | 7/1967 | Heifetz |
| 3,840,904 A | 10/1974 | Tronzo |
| 3,975,858 A | 8/1976 | Much |
| 4,246,895 A | 1/1981 | Rehder |
| 4,306,866 A | 12/1981 | Weissman |
| 4,324,006 A | 4/1982 | Charnley |
| 4,421,112 A | 12/1983 | Mains et al. |
| 4,436,684 A | 3/1984 | White |
| 4,457,306 A | 7/1984 | Borzone |
| 4,475,549 A | 10/1984 | Oh |
| 4,506,393 A | 3/1985 | Murphy |
| 4,524,766 A | 6/1985 | Petersen |
| 4,528,980 A | 7/1985 | Kenna |
| 4,565,191 A | 1/1986 | Slocum |
| 4,619,658 A | 10/1986 | Pappas et al. |
| 4,621,630 A | 11/1986 | Kenna |
| 4,632,111 A | 12/1986 | Roche |
| 4,633,862 A | 1/1987 | Petersen |
| 4,663,720 A | 5/1987 | Duret et al. |
| 4,689,984 A | 9/1987 | Kellner |
| 4,695,283 A | 9/1987 | Aldinger |
| 4,696,292 A | 9/1987 | Heiple |
| 4,703,751 A | 11/1987 | Pohl |
| 4,704,686 A | 11/1987 | Aldinger |
| 4,706,660 A | 11/1987 | Petersen |
| 4,719,907 A | 1/1988 | Banko et al. |
| 4,721,104 A | 1/1988 | Kaufman et al. |
| 4,722,330 A | 2/1988 | Russell et al. |
| 4,759,350 A | 7/1988 | Dunn et al. |
| 4,778,474 A | 10/1988 | Homsy |
| 4,800,874 A | 1/1989 | David et al. |
| 4,821,213 A | 4/1989 | Cline et al. |
| 4,822,365 A | 4/1989 | Walker et al. |
| 4,841,975 A | 6/1989 | Woolson |
| 4,846,161 A | 7/1989 | Roger |
| 4,871,975 A | 10/1989 | Nawata et al. |
| 4,892,545 A | 1/1990 | Day et al. |
| 4,893,619 A | 1/1990 | Dale et al. |
| 4,896,663 A | 1/1990 | Vandewalls |
| 4,907,577 A | 3/1990 | Wu |
| 4,927,422 A | 5/1990 | Engelhardt |
| 4,936,862 A | 6/1990 | Walker et al. |
| 4,952,213 A | 8/1990 | Bowman et al. |
| 4,959,066 A | 9/1990 | Dunn et al. |
| 4,976,737 A | 12/1990 | Leake |
| 4,979,949 A | 12/1990 | Matsen, III et al. |
| 4,985,037 A | 1/1991 | Petersen |
| 5,002,579 A | 3/1991 | Copf et al. |
| 5,006,121 A | 4/1991 | Hafeli |
| 5,007,936 A | 4/1991 | Woolson |
| 5,030,219 A | 7/1991 | Matsen et al. |
| 5,030,221 A | 7/1991 | Buechel et al. |
| 5,041,117 A | 8/1991 | Engelhardt |
| 5,053,037 A | 10/1991 | Lackey |
| 5,053,039 A | 10/1991 | Hofmann et al. |
| 5,056,351 A | 10/1991 | Stiver et al. |
| 5,086,401 A | 2/1992 | Glassman et al. |
| 5,098,383 A | 3/1992 | Hemmy et al. |
| 5,098,436 A | 3/1992 | Ferrante et al. |
| 5,108,425 A | 4/1992 | Hwang |
| 5,122,144 A | 6/1992 | Bert et al. |
| 5,123,927 A | 6/1992 | Duncan et al. |
| 5,129,908 A | 7/1992 | Petersen |
| 5,129,909 A | 7/1992 | Sutherland |
| 5,133,760 A | 7/1992 | Petersen et al. |
| 5,140,777 A | 8/1992 | Ushiyama et al. |
| 5,150,304 A | 9/1992 | Berchem et al. |
| 5,176,684 A | 1/1993 | Ferrante et al. |
| 5,194,066 A | 3/1993 | Van Zile |
| 5,234,433 A | 8/1993 | Bert et al. |
| 5,246,444 A | 9/1993 | Schreiber |
| 5,253,506 A | 10/1993 | Davis et al. |
| 5,258,032 A | 11/1993 | Bertin |
| 5,261,915 A | 11/1993 | Durlacher et al. |
| 5,274,565 A | 12/1993 | Reuben |
| 5,282,802 A | 2/1994 | Mahony, III |
| 5,299,288 A | 3/1994 | Glassman et al. |
| 5,300,077 A | 4/1994 | Howell |
| 5,320,529 A | 6/1994 | Pompa |
| 5,320,625 A | 6/1994 | Bertin |
| 5,323,697 A | 6/1994 | Schrock |
| 5,342,366 A | 8/1994 | Whiteside et al. |
| 5,344,423 A | 9/1994 | Dietz et al. |
| 5,360,446 A | 11/1994 | Kennedy |
| 5,364,402 A | 11/1994 | Mumme et al. |
| 5,368,858 A | 11/1994 | Hunziker |
| 5,370,692 A | 12/1994 | Fink et al. |
| 5,370,699 A | 12/1994 | Hood et al. |
| 5,405,395 A | 4/1995 | Coates |
| 5,408,409 A | 4/1995 | Glassman et al. |
| 5,411,521 A | 5/1995 | Putnam et al. |
| 5,415,662 A | 5/1995 | Ferrante et al. |
| 5,417,694 A | 5/1995 | Marik et al. |
| 5,438,263 A | 8/1995 | Dworkin et al. |
| 5,440,496 A | 8/1995 | Andersson et al. |
| 5,448,489 A | 9/1995 | Reuben |
| 5,449,360 A | 9/1995 | Schreiber |
| 5,452,407 A | 9/1995 | Crook |
| 5,454,816 A | 10/1995 | Ashby |
| 5,462,550 A | 10/1995 | Dietz et al. |
| 5,472,415 A | 12/1995 | King et al. |
| 5,474,559 A | 12/1995 | Bertin et al. |
| 5,490,854 A | 2/1996 | Fisher et al. |
| 5,496,324 A | 3/1996 | Barnes |
| 5,507,833 A | 4/1996 | Bohn |
| 5,514,519 A | 5/1996 | Neckers |
| 5,520,695 A | 5/1996 | Luckman |
| 5,527,317 A | 6/1996 | Ashby et al. |
| 5,539,649 A | 7/1996 | Walsh et al. |
| 5,540,695 A | 7/1996 | Levy |
| 5,545,222 A | 8/1996 | Bonutti |
| 5,549,688 A | 8/1996 | Ries et al. |
| 5,554,190 A | 9/1996 | Draenert |
| 5,560,096 A | 10/1996 | Stephens |
| 5,571,110 A | 11/1996 | Matsen, III et al. |
| 5,578,037 A | 11/1996 | Sanders et al. |
| 5,593,411 A | 1/1997 | Stalcup et al. |
| 5,595,703 A | 1/1997 | Swaelens et al. |
| 5,601,565 A | 2/1997 | Huebner |
| 5,607,431 A | 3/1997 | Dudasik et al. |
| 5,611,802 A | 3/1997 | Samuelson et al. |
| 5,613,969 A | 3/1997 | Jenkins, Jr. |
| 5,620,448 A | 4/1997 | Puddu |
| 5,634,927 A | 6/1997 | Houston et al. |
| 5,641,323 A | 6/1997 | Caldarise |
| 5,653,714 A | 8/1997 | Dietz et al. |
| 5,658,294 A | 8/1997 | Sederholm |
| 5,662,656 A | 9/1997 | White |
| 5,662,710 A | 9/1997 | Bonutti |
| 5,671,018 A | 9/1997 | Ohara et al. |
| 5,676,668 A | 10/1997 | McCue et al. |
| 5,677,107 A | 10/1997 | Neckers |
| 5,681,354 A | 10/1997 | Eckhoff |
| 5,682,886 A | 11/1997 | Delp et al. |
| 5,683,469 A | 11/1997 | Johnson et al. |
| 5,690,635 A | 11/1997 | Matsen, III et al. |
| 5,697,933 A | 12/1997 | Gundlapalli et al. |
| 5,702,460 A | 12/1997 | Carls et al. |
| 5,702,464 A | 12/1997 | Lackey et al. |
| 5,704,941 A | 1/1998 | Jacober et al. |
| 5,709,689 A | 1/1998 | Ferrante et al. |
| 5,720,752 A | 2/1998 | Elliot et al. |

(56) References Cited

U.S. PATENT DOCUMENTS

| | | |
|---|---|---|
| 5,722,978 A | 3/1998 | Jenkins, Jr. |
| 5,725,376 A | 3/1998 | Poirier |
| 5,725,593 A | 3/1998 | Caracciolo |
| 5,735,277 A | 4/1998 | Schuster |
| 5,745,834 A | 4/1998 | Bampton et al. |
| 5,748,767 A | 5/1998 | Raab |
| 5,749,875 A | 5/1998 | Puddu |
| 5,749,876 A | 5/1998 | Duvillier et al. |
| 5,762,125 A | 6/1998 | Mastrorio |
| 5,766,251 A | 6/1998 | Koshino |
| 5,768,134 A | 6/1998 | Swaelens et al. |
| 5,769,092 A | 6/1998 | Williamson, Jr. |
| 5,776,200 A | 7/1998 | Johnson et al. |
| 5,786,217 A | 7/1998 | Tubo et al. |
| 5,792,143 A | 8/1998 | Samuelson et al. |
| 5,798,924 A | 8/1998 | Eufinger et al. |
| 5,799,055 A | 8/1998 | Peshkin et al. |
| 5,835,619 A | 11/1998 | Morimoto et al. |
| 5,860,980 A | 1/1999 | Axelson, Jr. et al. |
| 5,860,981 A | 1/1999 | Bertin et al. |
| 5,871,018 A | 2/1999 | Delp et al. |
| 5,876,456 A | 3/1999 | Sederholm et al. |
| 5,879,398 A | 3/1999 | Swarts et al. |
| 5,879,402 A | 3/1999 | Lawes et al. |
| 5,880,976 A | 3/1999 | DiGioia III et al. |
| 5,885,297 A | 3/1999 | Matsen |
| 5,885,298 A | 3/1999 | Herrington et al. |
| 5,888,219 A | 3/1999 | Bonutti |
| 5,895,389 A | 4/1999 | Schenk et al. |
| 5,899,907 A | 5/1999 | Johnson |
| 5,901,060 A | 5/1999 | Schall et al. |
| 5,911,724 A | 6/1999 | Wehrli |
| 5,921,988 A | 7/1999 | Legrand |
| 5,925,049 A | 7/1999 | Gustilo et al. |
| 5,942,370 A | 8/1999 | Neckers |
| 5,967,777 A | 10/1999 | Klein et al. |
| 5,976,149 A | 11/1999 | Masini |
| 5,980,526 A | 11/1999 | Johnson et al. |
| 6,008,433 A | 12/1999 | Stone |
| 6,019,767 A | 2/2000 | Howell |
| 6,033,415 A | 3/2000 | Mittelstadt et al. |
| 6,042,612 A | 3/2000 | Voydeville |
| 6,056,754 A | 5/2000 | Haines et al. |
| 6,059,789 A | 5/2000 | Dinger |
| 6,059,833 A | 5/2000 | Doets |
| 6,066,175 A | 5/2000 | Henderson et al. |
| 6,086,593 A | 7/2000 | Bonutti |
| 6,120,510 A | 9/2000 | Albrektsson et al. |
| 6,120,544 A | 9/2000 | Grundei et al. |
| 6,126,690 A | 10/2000 | Ateshian et al. |
| 6,126,692 A | 10/2000 | Robie et al. |
| 6,136,033 A | 10/2000 | Suemer |
| 6,156,069 A | 12/2000 | Amstutz |
| 6,159,217 A | 12/2000 | Robie et al. |
| 6,161,080 A | 12/2000 | Aouni-Ateshian et al. |
| 6,162,257 A | 12/2000 | Gustilo et al. |
| 6,165,223 A | 12/2000 | Metzger et al. |
| 6,187,010 B1 | 2/2001 | Masini |
| 6,195,615 B1 | 2/2001 | Lysen |
| 6,203,546 B1 | 3/2001 | Macmahon |
| 6,205,411 B1 | 3/2001 | DiGioia, III et al. |
| 6,206,927 B1 | 3/2001 | Fell et al. |
| 6,210,445 B1 | 4/2001 | Zawadzki |
| 6,238,435 B1 | 5/2001 | Meulink et al. |
| 6,254,604 B1 | 7/2001 | Howell |
| 6,258,097 B1 | 7/2001 | Cook et al. |
| 6,264,698 B1 | 7/2001 | Lawes et al. |
| 6,270,529 B1 | 8/2001 | Terrill-Grisoni et al. |
| 6,273,891 B1 | 8/2001 | Masini |
| 6,290,727 B1 | 9/2001 | Otto et al. |
| 6,293,971 B1 | 9/2001 | Nelson et al. |
| 6,302,913 B1 | 10/2001 | Ripamonti et al. |
| 6,310,269 B1 | 10/2001 | Friese et al. |
| 6,312,258 B1 | 11/2001 | Ashman |
| 6,312,473 B1 | 11/2001 | Oshida |
| 6,319,285 B1 | 11/2001 | Chamier et al. |
| 6,322,728 B1 | 11/2001 | Brodkin et al. |
| 6,325,829 B1 | 12/2001 | Schmotzer |
| 6,327,491 B1 | 12/2001 | Franklin et al. |
| 6,338,738 B1 | 1/2002 | Bellotti et al. |
| 6,343,987 B2 | 2/2002 | Hayama et al. |
| 6,354,011 B1 | 3/2002 | Albrecht |
| 6,361,563 B2 | 3/2002 | Terrill-Grisoni et al. |
| 6,379,299 B1 | 4/2002 | Borodulin et al. |
| 6,379,388 B1 | 4/2002 | Ensign et al. |
| 6,383,228 B1 | 5/2002 | Schmotzer |
| 6,391,251 B1 | 5/2002 | Keicher et al. |
| 6,395,005 B1 | 5/2002 | Lovell |
| 6,413,279 B1 | 7/2002 | Metzger et al. |
| 6,424,332 B1 | 7/2002 | Powell |
| 6,427,698 B1 | 8/2002 | Yoon et al. |
| 6,459,948 B1 | 10/2002 | Ateshian et al. |
| 6,463,351 B1 | 10/2002 | Clynch |
| 6,475,243 B1 | 11/2002 | Sheldon et al. |
| 6,482,236 B2 | 11/2002 | Habecker |
| 6,488,715 B1 | 12/2002 | Pope et al. |
| 6,503,255 B1 | 1/2003 | Albrektsson et al. |
| 6,508,980 B1 | 1/2003 | Sachs et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,519,998 B2 | 2/2003 | Ertl et al. |
| 6,520,964 B2 | 2/2003 | Tallarida et al. |
| 6,533,737 B1 | 3/2003 | Brosseau et al. |
| 6,547,823 B2 | 4/2003 | Scarborough et al. |
| 6,551,325 B2 | 4/2003 | Neubauer et al. |
| 6,554,837 B1 | 4/2003 | Hauri et al. |
| 6,556,008 B2 | 4/2003 | Thesen |
| 6,558,391 B2 | 5/2003 | Axelson, Jr. et al. |
| 6,558,428 B2 | 5/2003 | Park |
| 6,562,073 B2 | 5/2003 | Foley |
| 6,564,085 B2 | 5/2003 | Meaney et al. |
| 6,567,681 B1 | 5/2003 | Lindequist |
| 6,575,980 B1 | 6/2003 | Robie et al. |
| 6,575,982 B1 | 6/2003 | Bonutti |
| 6,589,283 B1 | 7/2003 | Metzger et al. |
| 6,591,581 B2 | 7/2003 | Schmieding |
| 6,605,293 B1 | 8/2003 | Giordano et al. |
| 6,610,067 B2 | 8/2003 | Tallarida et al. |
| 6,622,567 B1 | 9/2003 | Hamel et al. |
| 6,629,999 B1 | 10/2003 | Serafin, Jr. |
| 6,641,617 B1 | 11/2003 | Merrill et al. |
| 6,676,892 B2 | 1/2004 | Das et al. |
| 6,682,566 B2 | 1/2004 | Draenert |
| 6,696,073 B2 | 2/2004 | Boyce et al. |
| 6,697,664 B2 | 2/2004 | Kienzle III et al. |
| 6,701,174 B1 | 3/2004 | Krause et al. |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,749,638 B1 | 6/2004 | Saladino |
| 6,750,653 B1 | 6/2004 | Zou et al. |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,823,871 B2 | 11/2004 | Schmieding |
| 6,827,723 B2 | 12/2004 | Carson |
| 6,887,247 B1 | 5/2005 | Couture et al. |
| 6,905,514 B2 | 6/2005 | Carignan et al. |
| 6,916,324 B2 | 7/2005 | Sanford |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 | 11/2005 | Kolb et al. |

(56) References Cited

U.S. PATENT DOCUMENTS

| | | |
|---|---|---|
| 6,975,755 B1 | 12/2005 | Baumberg |
| 6,990,220 B2 | 1/2006 | Ellis et al. |
| 6,993,406 B1 | 1/2006 | Cesarano, III et al. |
| 7,001,385 B2 | 2/2006 | Bonutti |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | Mckinnon |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,121,832 B2 | 10/2006 | Hsieh et al. |
| 7,141,053 B2 | 11/2006 | Rosa et al. |
| D533,664 S | 12/2006 | Büttler et al. |
| 7,169,185 B2 | 1/2007 | Sidebotham |
| 7,174,282 B2 | 2/2007 | Hollister et al. |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | Disilvestro et al. |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,275,218 B2 | 9/2007 | Petrella et al. |
| 7,282,054 B2 | 10/2007 | Steffensmeier et al. |
| 7,291,177 B2 | 11/2007 | Gibbs |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,231 B2 | 2/2008 | Mclean |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,390,327 B2 | 6/2008 | Collazo et al. |
| 7,392,076 B2 | 6/2008 | Moctezuma De La Barrera |
| 7,427,200 B2 | 9/2008 | Noble et al. |
| 7,427,272 B2 | 9/2008 | Richard et al. |
| 7,465,320 B1 | 12/2008 | Kito et al. |
| 7,468,075 B2 | 12/2008 | Lang et al. |
| 7,474,223 B2 | 1/2009 | Nycz et al. |
| 7,488,325 B2 | 2/2009 | Qian |
| 7,494,510 B2 | 2/2009 | Zweymuller |
| 7,517,365 B2 | 4/2009 | Carignan et al. |
| 7,519,540 B2 | 4/2009 | Mayaud |
| 7,527,631 B2 | 5/2009 | Maroney et al. |
| 7,534,263 B2 | 5/2009 | Burdulis, Jr. et al. |
| 7,537,664 B2 | 5/2009 | O'neill et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kelman |
| 7,601,155 B2 | 10/2009 | Petersen |
| 7,603,192 B2 | 10/2009 | Martin et al. |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,646,161 B2 | 1/2010 | Albu-Schäffer et al. |
| 7,651,501 B2 | 1/2010 | Penenberg et al. |
| 7,670,345 B2 | 3/2010 | Plassky et al. |
| 7,674,100 B2 | 3/2010 | Hayes-pankhurst et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,699,847 B2 | 4/2010 | Sheldon et al. |
| 7,704,253 B2 | 4/2010 | Bastian et al. |
| 7,723,395 B2 | 5/2010 | Ringeisen et al. |
| 7,747,305 B2 | 6/2010 | Dean et al. |
| D622,854 S | 8/2010 | Otto et al. |
| 7,780,672 B2 | 8/2010 | Metzger et al. |
| 7,780,740 B2 | 8/2010 | Steinberg |
| 7,789,885 B2 | 9/2010 | Metzger |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,833,245 B2 | 11/2010 | Kaes et al. |
| 7,837,040 B2 | 11/2010 | Ward et al. |
| 7,837,690 B2 | 11/2010 | Metzger |
| 7,846,382 B2 | 12/2010 | Strand |
| 7,850,698 B2 | 12/2010 | Straszheim-Morley et al. |
| 7,879,109 B2 | 2/2011 | Borden et al. |
| 7,892,261 B2 | 2/2011 | Bonutti |
| 7,896,921 B2 | 3/2011 | Smith et al. |
| 7,926,363 B2 | 4/2011 | Miller et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,988,736 B2 | 8/2011 | May et al. |
| 7,993,353 B2 | 8/2011 | Roßner et al. |
| 8,062,301 B2 | 11/2011 | Ammann et al. |
| 8,066,708 B2 | 11/2011 | Lang et al. |
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,105,330 B2 | 1/2012 | Fitz et al. |
| 8,122,582 B2 | 2/2012 | Burdulis, Jr. et al. |
| 8,133,230 B2 | 3/2012 | Stevens et al. |
| 8,133,234 B2 | 3/2012 | Meridew et al. |
| 8,137,406 B2 | 3/2012 | Novak et al. |
| 8,147,861 B2 | 4/2012 | Jones et al. |
| 8,160,345 B2 | 4/2012 | Pavlovskaia et al. |
| 8,167,951 B2 | 5/2012 | Ammann et al. |
| 8,170,641 B2 | 5/2012 | Belcher |
| 8,182,489 B2 | 5/2012 | Horacek |
| 8,192,441 B2 | 6/2012 | Collazo |
| 8,192,495 B2 | 6/2012 | Simpson et al. |
| 8,200,355 B2 | 6/2012 | Lee et al. |
| 8,211,112 B2 | 7/2012 | Novak et al. |
| 8,221,430 B2 | 7/2012 | Park et al. |
| 8,241,292 B2 | 8/2012 | Collazo |
| 8,241,293 B2 | 8/2012 | Stone et al. |
| 8,246,680 B2 | 8/2012 | Betz et al. |
| 8,260,589 B1 | 9/2012 | Kumar |
| 8,265,790 B2 | 9/2012 | Amiot et al. |
| 8,268,099 B2 | 9/2012 | O'neill et al. |
| 8,268,100 B2 | 9/2012 | O'neill et al. |
| D669,176 S | 10/2012 | Frey |
| 8,282,646 B2 | 10/2012 | Schoenefeld et al. |
| 8,298,237 B2 | 10/2012 | Schoenefeld et al. |
| 8,303,596 B2 | 11/2012 | Plaßky et al. |
| 8,313,491 B2 | 11/2012 | Green, II et al. |
| D672,038 S | 12/2012 | Frey |
| 8,333,772 B2 | 12/2012 | Fox et al. |
| 8,337,503 B2 | 12/2012 | Lian |
| 8,355,773 B2 | 1/2013 | Leitner et al. |
| 8,372,078 B2 | 2/2013 | Collazo |
| 8,377,066 B2 | 2/2013 | Katrana et al. |
| 8,388,690 B2 | 3/2013 | Singhatat et al. |
| 8,398,646 B2 | 3/2013 | Metzger et al. |
| 8,407,067 B2 | 3/2013 | Uthgenannt et al. |
| 8,414,594 B2 | 4/2013 | Berger et al. |

(56) References Cited

U.S. PATENT DOCUMENTS

| | | |
|---|---|---|
| 8,419,741 B2 | 4/2013 | Carignan et al. |
| 8,425,522 B2 | 4/2013 | Bonutti |
| 8,430,882 B2 | 4/2013 | Lowry et al. |
| 8,430,931 B2 | 4/2013 | Acker et al. |
| 8,439,675 B2 | 5/2013 | De Moyer |
| 8,439,925 B2 | 5/2013 | Marino et al. |
| 8,444,564 B2 | 5/2013 | Mahfouz et al. |
| 8,444,651 B2 | 5/2013 | Kunz et al. |
| 8,457,930 B2 | 6/2013 | Schroeder |
| 8,460,302 B2 | 6/2013 | Park et al. |
| 8,469,961 B2 | 6/2013 | Alleyne et al. |
| 8,473,305 B2 | 6/2013 | Belcher et al. |
| 8,486,150 B2 | 7/2013 | White et al. |
| 8,500,740 B2 | 8/2013 | Bojarski et al. |
| 8,532,361 B2 | 9/2013 | Pavlovskaia et al. |
| 8,532,806 B1 | 9/2013 | Masson |
| 8,532,807 B2 | 9/2013 | Metzger |
| 8,535,387 B2 | 9/2013 | Meridew et al. |
| 8,543,234 B2 | 9/2013 | Gao |
| 8,545,508 B2 | 10/2013 | Collazo |
| 8,568,487 B2 | 10/2013 | Witt et al. |
| 8,591,516 B2 | 11/2013 | Metzger et al. |
| 8,597,365 B2 | 12/2013 | Meridew |
| 8,603,180 B2 | 12/2013 | White et al. |
| 8,608,748 B2 | 12/2013 | Metzger et al. |
| 8,608,749 B2 | 12/2013 | Meridew et al. |
| 8,617,170 B2 | 12/2013 | Ashby et al. |
| 8,617,174 B2 | 12/2013 | Axelson, Jr. et al. |
| 8,617,175 B2 | 12/2013 | Park et al. |
| 8,632,547 B2 | 1/2014 | Maxson et al. |
| 8,652,142 B2 | 2/2014 | Geissler |
| 8,668,700 B2 | 3/2014 | Catanzarite et al. |
| 8,702,712 B2 | 4/2014 | Jordan et al. |
| 8,702,715 B2 | 4/2014 | Ammann et al. |
| 8,706,285 B2 | 4/2014 | Narainasamy et al. |
| 8,715,289 B2 | 5/2014 | Smith |
| 8,728,387 B2 | 5/2014 | Jones et al. |
| 8,735,773 B2 | 5/2014 | Lang |
| 8,764,760 B2 | 7/2014 | Metzger et al. |
| 8,775,133 B2 | 7/2014 | Schroeder |
| 8,777,875 B2 | 7/2014 | Park |
| 8,828,016 B2 | 9/2014 | Major et al. |
| 8,828,087 B2 | 9/2014 | Stone et al. |
| 8,828,089 B1 | 9/2014 | Perez et al. |
| 8,834,568 B2 | 9/2014 | Shapiro |
| 8,858,561 B2 | 10/2014 | White et al. |
| 8,864,769 B2 | 10/2014 | Stone et al. |
| 8,900,244 B2 | 12/2014 | Meridew et al. |
| 8,903,530 B2 | 12/2014 | Metzger |
| 8,956,364 B2 | 2/2015 | Catanzarite |
| 8,979,936 B2 | 3/2015 | White et al. |
| 9,005,297 B2 | 4/2015 | Katrana et al. |
| 2001/0005797 A1 | 6/2001 | Barlow et al. |
| 2001/0011190 A1 | 8/2001 | Park |
| 2001/0021876 A1 | 9/2001 | Terrill-Grisoni et al. |
| 2001/0054478 A1 | 12/2001 | Watanabe et al. |
| 2002/0007294 A1 | 1/2002 | Bradbury et al. |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0092532 A1 | 7/2002 | Yoon |
| 2002/0107522 A1 | 8/2002 | Picard et al. |
| 2002/0128872 A1 | 9/2002 | Giammattei |
| 2002/0147415 A1 | 10/2002 | Martelli |
| 2002/0186818 A1 | 12/2002 | Arnaud et al. |
| 2002/0193797 A1 | 12/2002 | Johnson et al. |
| 2002/0198528 A1 | 12/2002 | Engh et al. |
| 2002/0198531 A1 | 12/2002 | Millard et al. |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson, Jr. et al. |
| 2003/0039676 A1 | 2/2003 | Boyce et al. |
| 2003/0055502 A1 | 3/2003 | Lang et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0130741 A1 | 7/2003 | McMinn |
| 2003/0139817 A1 | 7/2003 | Tuke et al. |
| 2003/0158606 A1 | 8/2003 | Coon et al. |
| 2003/0171757 A1 | 9/2003 | Coon et al. |
| 2003/0216669 A1 | 11/2003 | Lang et al. |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0054416 A1 | 3/2004 | Wyss et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122436 A1 | 6/2004 | Grimm |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0193169 A1 | 9/2004 | Schon et al. |
| 2004/0204644 A1 | 10/2004 | Tsougarakis et al. |
| 2004/0204760 A1 | 10/2004 | Fitz et al. |
| 2004/0212586 A1 | 10/2004 | Trueman, III |
| 2004/0220583 A1 | 11/2004 | Pieczynski, II et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | De La Barrera |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0148843 A1 | 7/2005 | Roose |
| 2005/0149042 A1 | 7/2005 | Metzger |
| 2005/0171545 A1 | 8/2005 | Walsh et al. |
| 2005/0177245 A1 | 8/2005 | Leatherbury et al. |
| 2005/0203536 A1 | 9/2005 | Laffargue et al. |
| 2005/0203540 A1 | 9/2005 | Broyles |
| 2005/0209605 A1 | 9/2005 | Grimm et al. |
| 2005/0216305 A1 | 9/2005 | Funderud |
| 2005/0222571 A1 | 10/2005 | Ryan |
| 2005/0222573 A1 | 10/2005 | Branch et al. |

(56) References Cited

U.S. PATENT DOCUMENTS

| | | |
|---|---|---|
| 2005/0228393 A1 | 10/2005 | Williams, III et al. |
| 2005/0234461 A1 | 10/2005 | Burdulis, Jr. et al. |
| 2005/0234465 A1 | 10/2005 | Mccombs et al. |
| 2005/0234468 A1 | 10/2005 | Carson |
| 2005/0240195 A1 | 10/2005 | Axelson, Jr. et al. |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis, Jr. et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady, Jr. et al. |
| 2006/0100832 A1 | 5/2006 | Bowman |
| 2006/0105011 A1 | 5/2006 | Sun et al. |
| 2006/0111722 A1 | 5/2006 | Bouadi |
| 2006/0122616 A1 | 6/2006 | Bennett et al. |
| 2006/0122618 A1 | 6/2006 | Claypool et al. |
| 2006/0136058 A1 | 6/2006 | Pietrzak |
| 2006/0142657 A1 | 6/2006 | Quaid et al. |
| 2006/0147332 A1 | 7/2006 | Jones et al. |
| 2006/0149283 A1 | 7/2006 | May et al. |
| 2006/0155380 A1 | 7/2006 | Clemow et al. |
| 2006/0161165 A1 | 7/2006 | Swanson et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0184250 A1 | 8/2006 | Bandoh et al. |
| 2006/0190086 A1 | 8/2006 | Clemow et al. |
| 2006/0192319 A1 | 8/2006 | Solar |
| 2006/0195111 A1 | 8/2006 | Couture |
| 2006/0195194 A1 | 8/2006 | Gunther |
| 2006/0195198 A1 | 8/2006 | James |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0287891 A1 | 12/2006 | Grasso et al. |
| 2006/0293681 A1 | 12/2006 | Claypool et al. |
| 2007/0015995 A1 | 1/2007 | Lang et al. |
| 2007/0016008 A1 | 1/2007 | Schoenefeld |
| 2007/0016209 A1 | 1/2007 | Ammann et al. |
| 2007/0027680 A1 | 2/2007 | Ashley et al. |
| 2007/0039205 A1 | 2/2007 | Erb et al. |
| 2007/0043582 A1 | 2/2007 | Peveto et al. |
| 2007/0066917 A1 | 3/2007 | Hodorek et al. |
| 2007/0073133 A1 | 3/2007 | Schoenefeld |
| 2007/0073136 A1 | 3/2007 | Metzger |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0106299 A1 | 5/2007 | Manspeizer |
| 2007/0118055 A1 | 5/2007 | Mccombs |
| 2007/0118138 A1 | 5/2007 | Seo et al. |
| 2007/0118243 A1 | 5/2007 | Schroeder et al. |
| 2007/0129809 A1 | 6/2007 | Meridew et al. |
| 2007/0142914 A1 | 6/2007 | Jones et al. |
| 2007/0150068 A1 | 6/2007 | Dong et al. |
| 2007/0156066 A1 | 7/2007 | Mcginley et al. |
| 2007/0156171 A1 | 7/2007 | Lang et al. |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones |
| 2007/0198022 A1 | 8/2007 | Lang et al. |
| 2007/0203430 A1 | 8/2007 | Lang et al. |
| 2007/0203605 A1 | 8/2007 | Melton et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor, III et al. |
| 2007/0239481 A1 | 10/2007 | Disilvestro et al. |
| 2007/0244487 A1 | 10/2007 | Ammann et al. |
| 2007/0250169 A1 | 10/2007 | Lang |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0262867 A1 | 11/2007 | Westrick et al. |
| 2007/0272747 A1 | 11/2007 | Woods et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0288029 A1 | 12/2007 | Justin et al. |
| 2007/0288030 A1 | 12/2007 | Metzger et al. |
| 2008/0009952 A1 | 1/2008 | Hodge |
| 2008/0015599 A1 | 1/2008 | D'alessio et al. |
| 2008/0015603 A1 | 1/2008 | Collazo |
| 2008/0015604 A1 | 1/2008 | Collazo |
| 2008/0015605 A1 | 1/2008 | Collazo |
| 2008/0021299 A1 | 1/2008 | Meulink |
| 2008/0021494 A1 | 1/2008 | Schmelzeisen-redeker et al. |
| 2008/0021567 A1 | 1/2008 | Meulink et al. |
| 2008/0027563 A1 | 1/2008 | Johnson et al. |
| 2008/0033442 A1 | 2/2008 | Amiot et al. |
| 2008/0039850 A1 | 2/2008 | Rowley et al. |
| 2008/0051799 A1 | 2/2008 | Bonutti et al. |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0062183 A1 | 3/2008 | Swaelens |
| 2008/0065225 A1 | 3/2008 | Wasielewski et al. |
| 2008/0094396 A1 | 4/2008 | Sabczynsdi et al. |
| 2008/0097451 A1 | 4/2008 | Chen et al. |
| 2008/0112996 A1 | 5/2008 | Harlow et al. |
| 2008/0114370 A1 | 5/2008 | Schoenefeld |
| 2008/0133022 A1 | 6/2008 | Caylor |
| 2008/0140081 A1 | 6/2008 | Heavener et al. |
| 2008/0140209 A1 | 6/2008 | Iannotti et al. |
| 2008/0140213 A1 | 6/2008 | Ammann et al. |
| 2008/0146969 A1 | 6/2008 | Kurtz |
| 2008/0147072 A1 | 6/2008 | Park et al. |
| 2008/0147073 A1 | 6/2008 | Ammann et al. |
| 2008/0147074 A1 | 6/2008 | Ammann et al. |
| 2008/0161815 A1 | 7/2008 | Schoenefeld et al. |
| 2008/0161816 A1 | 7/2008 | Stevens et al. |
| 2008/0172125 A1 | 7/2008 | Ek |
| 2008/0195099 A1 | 8/2008 | Minas |
| 2008/0195107 A1 | 8/2008 | Cuckler et al. |

(56) References Cited

U.S. PATENT DOCUMENTS

| | | |
|---|---|---|
| 2008/0195108 A1 | 8/2008 | Bhatnagar et al. |
| 2008/0195109 A1 | 8/2008 | Hunter et al. |
| 2008/0195216 A1 | 8/2008 | Philipp |
| 2008/0200926 A1 | 8/2008 | Verard et al. |
| 2008/0208200 A1 | 8/2008 | Crofford |
| 2008/0208353 A1 | 8/2008 | Kumar et al. |
| 2008/0215059 A1 | 9/2008 | Carignan et al. |
| 2008/0230422 A1 | 9/2008 | Pleil et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0255674 A1 | 10/2008 | Rahaman et al. |
| 2008/0257363 A1 | 10/2008 | Schoenefeld et al. |
| 2008/0262500 A1 | 10/2008 | Collazo |
| 2008/0262624 A1 | 10/2008 | White et al. |
| 2008/0269596 A1 | 10/2008 | Revie et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287926 A1 | 11/2008 | Abou El Kheir |
| 2008/0287954 A1 | 11/2008 | Kunz et al. |
| 2008/0294170 A1 | 11/2008 | O'brien |
| 2008/0294266 A1 | 11/2008 | Steinberg |
| 2008/0300600 A1 | 12/2008 | Guelat et al. |
| 2008/0306485 A1 | 12/2008 | Coon et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0018666 A1 | 1/2009 | Grundei et al. |
| 2009/0024131 A1 | 1/2009 | Metzger et al. |
| 2009/0024169 A1 | 1/2009 | Triplett et al. |
| 2009/0043556 A1 | 2/2009 | Axelson et al. |
| 2009/0048618 A1 | 2/2009 | Harrison et al. |
| 2009/0066936 A1 | 3/2009 | Huang et al. |
| 2009/0076371 A1 | 3/2009 | Lang et al. |
| 2009/0076512 A1 | 3/2009 | Ammann et al. |
| 2009/0076520 A1 | 3/2009 | Choi |
| 2009/0076555 A1 | 3/2009 | Lowry et al. |
| 2009/0082770 A1 | 3/2009 | Womer et al. |
| 2009/0082774 A1 | 3/2009 | Oti et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0088865 A1 | 4/2009 | Brehm |
| 2009/0088866 A1 | 4/2009 | Case |
| 2009/0089034 A1 | 4/2009 | Penney et al. |
| 2009/0089081 A1 | 4/2009 | Haddad |
| 2009/0093815 A1 | 4/2009 | Fletcher et al. |
| 2009/0093816 A1 | 4/2009 | Roose et al. |
| 2009/0096613 A1 | 4/2009 | Westrick |
| 2009/0099567 A1 | 4/2009 | Zajac |
| 2009/0105837 A1 | 4/2009 | Lafosse et al. |
| 2009/0116621 A1 | 5/2009 | Yuan et al. |
| 2009/0118736 A1 | 5/2009 | Kreuzer |
| 2009/0118769 A1 | 5/2009 | Sixto, Jr. et al. |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0149964 A1 | 6/2009 | May et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0177282 A1 | 7/2009 | Bureau et al. |
| 2009/0187193 A1 | 7/2009 | Maroney et al. |
| 2009/0209884 A1 | 8/2009 | Van Vorhis et al. |
| 2009/0209961 A1 | 8/2009 | Ferrante et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0222103 A1 | 9/2009 | Fitz et al. |
| 2009/0226068 A1 | 9/2009 | Fitz et al. |
| 2009/0228016 A1 | 9/2009 | Alvarez |
| 2009/0234360 A1 | 9/2009 | Alexander |
| 2009/0248044 A1 | 10/2009 | Amiot et al. |
| 2009/0250413 A1 | 10/2009 | Hoeppner |
| 2009/0254093 A1 | 10/2009 | White et al. |
| 2009/0254367 A1 | 10/2009 | Belcher et al. |
| 2009/0259312 A1 | 10/2009 | Shterling et al. |
| 2009/0264889 A1 | 10/2009 | Long et al. |
| 2009/0270868 A1 | 10/2009 | Park et al. |
| 2009/0274350 A1 | 11/2009 | Pavlovskaia et al. |
| 2009/0287217 A1 | 11/2009 | Ammann et al. |
| 2009/0287309 A1 | 11/2009 | Walch et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1 | 12/2009 | White et al. |
| 2010/0010493 A1 | 1/2010 | Dower |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0036404 A1 | 2/2010 | Yi et al. |
| 2010/0042105 A1 | 2/2010 | Park et al. |
| 2010/0049195 A1 | 2/2010 | Park et al. |
| 2010/0057088 A1 | 3/2010 | Shah |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0082067 A1 | 4/2010 | Kondrashov |
| 2010/0087829 A1 | 4/2010 | Metzger |
| 2010/0094295 A1 | 4/2010 | Schnieders et al. |
| 2010/0105011 A1 | 4/2010 | Karkar et al. |
| 2010/0121334 A1 | 5/2010 | Couture et al. |
| 2010/0121335 A1 | 5/2010 | Penenberg et al. |
| 2010/0137869 A1 | 6/2010 | Borja et al. |
| 2010/0137924 A1 | 6/2010 | Tuke et al. |
| 2010/0139377 A1 | 6/2010 | Huang et al. |
| 2010/0145343 A1 | 6/2010 | Johnson et al. |
| 2010/0145344 A1 | 6/2010 | Jordan et al. |
| 2010/0152782 A1 | 6/2010 | Stone et al. |
| 2010/0160917 A1 | 6/2010 | Fitz et al. |
| 2010/0160919 A1 | 6/2010 | Axelson, Jr. et al. |
| 2010/0168752 A1 | 7/2010 | Edwards |
| 2010/0168754 A1 | 7/2010 | Fitz et al. |
| 2010/0168857 A1 | 7/2010 | Hatch |
| 2010/0168866 A1 | 7/2010 | Shih |
| 2010/0179663 A1 | 7/2010 | Steinberg |
| 2010/0185202 A1 | 7/2010 | Lester et al. |
| 2010/0191244 A1 | 7/2010 | White et al. |
| 2010/0198067 A1 | 8/2010 | Mahfouz et al. |
| 2010/0198224 A1 | 8/2010 | Metzger et al. |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0217399 A1 | 8/2010 | Groh |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0256649 A1 | 10/2010 | Capsal et al. |
| 2010/0262150 A1 | 10/2010 | Lian |
| 2010/0274253 A1 | 10/2010 | Ure |

(56) References Cited

U.S. PATENT DOCUMENTS

| | | |
|---|---|---|
| 2010/0281678 A1 | 11/2010 | Burdulis, Jr. et al. |
| 2010/0286700 A1 | 11/2010 | Snider et al. |
| 2010/0291401 A1 | 11/2010 | Medina et al. |
| 2010/0292743 A1 | 11/2010 | Singhal et al. |
| 2010/0298894 A1 | 11/2010 | Bojarski et al. |
| 2010/0305574 A1 | 12/2010 | Fitz et al. |
| 2010/0318088 A1 | 12/2010 | Warne et al. |
| 2010/0324692 A1 | 12/2010 | Uthgenannt et al. |
| 2011/0004317 A1 | 1/2011 | Hacking et al. |
| 2011/0008754 A1 | 1/2011 | Bassett et al. |
| 2011/0009869 A1 | 1/2011 | Marino et al. |
| 2011/0014081 A1 | 1/2011 | Jones et al. |
| 2011/0015636 A1 | 1/2011 | Katrana et al. |
| 2011/0015639 A1 | 1/2011 | Metzger et al. |
| 2011/0015752 A1 | 1/2011 | Meridew |
| 2011/0016690 A1 | 1/2011 | Narainasamy et al. |
| 2011/0022049 A1 | 1/2011 | Huebner et al. |
| 2011/0022174 A1 | 1/2011 | Holdstein et al. |
| 2011/0029088 A1 | 2/2011 | Rauscher et al. |
| 2011/0029091 A1 | 2/2011 | Bojarski et al. |
| 2011/0029093 A1 | 2/2011 | Bojarski |
| 2011/0029116 A1 | 2/2011 | Jordan et al. |
| 2011/0035012 A1 | 2/2011 | Linares |
| 2011/0040303 A1 | 2/2011 | Iannotti et al. |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0071581 A1 | 3/2011 | Lang et al. |
| 2011/0071802 A1 | 3/2011 | Bojarski et al. |
| 2011/0087332 A1 | 4/2011 | Bojarski et al. |
| 2011/0092804 A1 | 4/2011 | Schoenefeld et al. |
| 2011/0093086 A1 | 4/2011 | Witt et al. |
| 2011/0106093 A1 | 5/2011 | Romano et al. |
| 2011/0106254 A1 | 5/2011 | Abel et al. |
| 2011/0125264 A1 | 5/2011 | Bagga et al. |
| 2011/0125284 A1 | 5/2011 | Gabbrielli et al. |
| 2011/0130795 A1 | 6/2011 | Ball |
| 2011/0151027 A1 | 6/2011 | Clineff et al. |
| 2011/0151259 A1 | 6/2011 | Jarman-smith et al. |
| 2011/0153025 A1 | 6/2011 | Mcminn |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0177590 A1 | 7/2011 | Clyne et al. |
| 2011/0184419 A1 | 7/2011 | Meridew et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1 | 9/2011 | Maxson et al. |
| 2011/0214279 A1 | 9/2011 | Park et al. |
| 2011/0218545 A1 | 9/2011 | Catanzarite et al. |
| 2011/0224674 A1 | 9/2011 | White et al. |
| 2011/0238071 A1 | 9/2011 | Fernandez-scoma |
| 2011/0245835 A1 | 10/2011 | Dodds et al. |
| 2011/0251617 A1 | 10/2011 | Ammann et al. |
| 2011/0257657 A1 | 10/2011 | Turner et al. |
| 2011/0269100 A1 | 11/2011 | Furrer et al. |
| 2011/0275032 A1 | 11/2011 | Tardieu et al. |
| 2011/0276145 A1 | 11/2011 | Carignan et al. |
| 2011/0282473 A1 | 11/2011 | Pavlovskaia et al. |
| 2011/0295887 A1 | 12/2011 | Palmese et al. |
| 2011/0313424 A1 | 12/2011 | Bono et al. |
| 2011/0319745 A1 | 12/2011 | Frey |
| 2012/0010619 A1 | 1/2012 | Barsoum |
| 2012/0010710 A1 | 1/2012 | Frigg |
| 2012/0010711 A1 | 1/2012 | Antonyshyn et al. |
| 2012/0029345 A1 | 2/2012 | Mahfouz et al. |
| 2012/0029520 A1 | 2/2012 | Lang et al. |
| 2012/0041445 A1 | 2/2012 | Roose et al. |
| 2012/0041446 A1 | 2/2012 | Wong et al. |
| 2012/0041564 A1 | 2/2012 | Landon |
| 2012/0065640 A1 | 3/2012 | Metzger et al. |
| 2012/0078254 A1 | 3/2012 | Ashby et al. |
| 2012/0078258 A1 | 3/2012 | Lo et al. |
| 2012/0078259 A1 | 3/2012 | Meridew |
| 2012/0089595 A1 | 4/2012 | Jaecksch |
| 2012/0101586 A1 | 4/2012 | Carson |
| 2012/0109137 A1 | 5/2012 | Iannotti et al. |
| 2012/0109138 A1 | 5/2012 | Meridew et al. |
| 2012/0109226 A1 | 5/2012 | Iannotti et al. |
| 2012/0116203 A1 | 5/2012 | Vancraen et al. |
| 2012/0123422 A1 | 5/2012 | Agnihotri et al. |
| 2012/0130382 A1 | 5/2012 | Iannotti et al. |
| 2012/0136365 A1 | 5/2012 | Iannotti et al. |
| 2012/0141034 A1 | 6/2012 | Iannotti et al. |
| 2012/0143197 A1 | 6/2012 | Lang et al. |
| 2012/0143267 A1 | 6/2012 | Iannotti et al. |
| 2012/0150242 A1 | 6/2012 | Mannion |
| 2012/0158002 A1 | 6/2012 | Carignan et al. |
| 2012/0165954 A1 | 6/2012 | Nimal |
| 2012/0192401 A1 | 8/2012 | Pavlovskaia et al. |
| 2012/0196314 A1 | 8/2012 | Nawaz et al. |
| 2012/0209276 A1 | 8/2012 | Schuster |
| 2012/0215225 A1 | 8/2012 | Philippon et al. |
| 2012/0215310 A1 | 8/2012 | Sharp et al. |
| 2012/0221017 A1 | 8/2012 | Bonutti |
| 2012/0226283 A1 | 9/2012 | Meridew et al. |
| 2012/0232596 A1 | 9/2012 | Ribeiro |
| 2012/0245587 A1 | 9/2012 | Fang et al. |
| 2012/0259335 A1 | 10/2012 | Scifert et al. |
| 2012/0265208 A1 | 10/2012 | Smith |
| 2012/0271131 A1 | 10/2012 | Kling et al. |
| 2012/0271314 A1 | 10/2012 | Stemniski et al. |
| 2012/0271366 A1 | 10/2012 | Katrana et al. |
| 2012/0276509 A1 | 11/2012 | Iannotti et al. |
| 2012/0277751 A1 | 11/2012 | Catanzarite et al. |
| 2012/0289965 A1 | 11/2012 | Gelaude et al. |
| 2012/0296339 A1 | 11/2012 | Iannotti et al. |
| 2012/0303004 A1 | 11/2012 | Uthgenannt et al. |
| 2012/0303033 A1 | 11/2012 | Weiner et al. |
| 2012/0310364 A1 | 12/2012 | Li et al. |
| 2012/0310399 A1 | 12/2012 | Metzger |
| 2012/0316564 A1 | 12/2012 | Serbousek et al. |
| 2012/0323246 A1 | 12/2012 | Catanzarite et al. |
| 2012/0323282 A1 | 12/2012 | Brianza et al. |
| 2012/0323323 A1 | 12/2012 | Vargas et al. |
| 2013/0001121 A1 | 1/2013 | Metzger |
| 2013/0006250 A1 | 1/2013 | Metzger et al. |
| 2013/0018483 A1 | 1/2013 | Li et al. |
| 2013/0035766 A1 | 2/2013 | Meridew |
| 2013/0046310 A1 | 2/2013 | Ranawat et al. |
| 2013/0053854 A1 | 2/2013 | Schoenefeld et al. |
| 2013/0056912 A1 | 3/2013 | O'neill et al. |
| 2013/0060253 A1 | 3/2013 | Couture et al. |
| 2013/0072940 A1 | 3/2013 | Dawood et al. |
| 2013/0085500 A1 | 4/2013 | Meridew et al. |
| 2013/0085590 A1 | 4/2013 | Bryan et al. |
| 2013/0119579 A1 | 5/2013 | Iannotti et al. |
| 2013/0123850 A1 | 5/2013 | Schoenefeld et al. |
| 2013/0131681 A1 | 5/2013 | Katrana et al. |
| 2013/0144392 A1 | 6/2013 | Hughes |
| 2013/0197528 A1 | 8/2013 | Zakaria et al. |
| 2013/0197529 A1 | 8/2013 | Metzger |
| 2013/0197687 A1 | 8/2013 | Pavlovskaia et al. |
| 2013/0218163 A1 | 8/2013 | Frey |
| 2013/0245631 A1 | 9/2013 | Bettenga |
| 2013/0245801 A1 | 9/2013 | Schroeder |
| 2013/0261503 A1 | 10/2013 | Sherman |
| 2013/0264749 A1 | 10/2013 | Jones et al. |
| 2013/0268085 A1 | 10/2013 | Dong |
| 2013/0289730 A1 | 10/2013 | Gabriel et al. |
| 2013/0317511 A1 | 11/2013 | Bojarski et al. |
| 2013/0326878 A1 | 12/2013 | Boehm et al. |
| 2013/0338673 A1 | 12/2013 | Keppler |
| 2014/0005672 A1 | 1/2014 | Edwards et al. |
| 2014/0012266 A1 | 1/2014 | Bonin, Jr. et al. |

(56) References Cited

U.S. PATENT DOCUMENTS

| | | |
|---|---|---|
| 2014/0052270 A1 | 2/2014 | Witt et al. |
| 2014/0066937 A1 | 3/2014 | Wiebe, III et al. |
| 2014/0081659 A1 | 3/2014 | Nawana et al. |
| 2014/0088724 A1 | 3/2014 | Meridew |
| 2014/0094816 A1 | 4/2014 | White et al. |
| 2014/0100578 A1 | 4/2014 | Metzger et al. |
| 2014/0107651 A1 | 4/2014 | Meridew et al. |
| 2014/0107654 A1 | 4/2014 | Kehres et al. |
| 2014/0107715 A1 | 4/2014 | Heilman et al. |
| 2014/0081275 A1 | 5/2014 | Metzger et al. |
| 2014/0127211 A1 | 5/2014 | Geles et al. |
| 2014/0135775 A1 | 5/2014 | Maxson |
| 2014/0163564 A1 | 6/2014 | Bollinger |
| 2014/0163565 A1 | 6/2014 | Bollinger |
| 2014/0172116 A1 | 6/2014 | Maxson et al. |
| 2014/0180295 A1 | 6/2014 | Buza et al. |
| 2014/0188119 A1 | 7/2014 | Catanzarite et al. |
| 2014/0222157 A1 | 8/2014 | Al Hares et al. |
| 2014/0243833 A1 | 8/2014 | Smith |
| 2014/0257304 A1 | 9/2014 | Eash |
| 2014/0257508 A1 | 9/2014 | Bojarski et al. |
| 2014/0276854 A1 | 9/2014 | Schoenefeld et al. |
| 2014/0276856 A1 | 9/2014 | Schoenefeld |
| 2014/0276870 A1 | 9/2014 | Eash |
| 2014/0276873 A1 | 9/2014 | Meridew et al. |
| 2014/0303938 A1 | 10/2014 | Schoenefeld et al. |
| 2014/0303990 A1 | 10/2014 | Schoenefeld et al. |
| 2014/0309644 A1 | 10/2014 | Metzger et al. |
| 2014/0324058 A1 | 10/2014 | Metzger et al. |
| 2014/0378979 A1 | 12/2014 | Stone et al. |
| 2015/0088293 A1 | 3/2015 | Metzger |
| 2015/0112348 A1 | 4/2015 | Schoenefeld et al. |
| 2015/0112349 A1 | 4/2015 | Schoenefeld |
| 2015/0320430 A1 | 11/2015 | Kehres et al. |
| 2016/0374696 A1 | 12/2016 | Kehres et al. |
| 2019/0150958 A1 | 5/2019 | Kehres et al. |

FOREIGN PATENT DOCUMENTS

| | | |
|---|---|---|
| CA | 2505371 A1 | 5/2004 |
| CA | 2505419 A1 | 6/2004 |
| CA | 2506849 A1 | 6/2004 |
| CA | 2545965 A1 | 6/2005 |
| CA | 2546958 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 102038553 A | 5/2011 |
| CN | 102335742 A | 2/2012 |
| CN | 108124422 | 6/2018 |
| DE | 3447365 A1 | 7/1986 |
| DE | 04219939 A1 | 12/1993 |
| DE | 4421153 A1 | 12/1995 |
| DE | 10341187 A1 | 3/2005 |
| DE | 102009028503 A1 | 2/2011 |
| DE | 102011082902 A1 | 3/2012 |
| DE | 102012205820 A1 | 10/2012 |
| DE | 112010003901 T5 | 11/2012 |
| EP | 0114505 A1 | 8/1984 |
| EP | 0255797 A1 | 2/1988 |
| EP | 0326768 A2 | 8/1989 |
| EP | 0579868 A2 | 1/1994 |
| EP | 0591985 A1 | 4/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1634551 A2 | 3/2006 |
| EP | 1832239 A1 | 9/2007 |
| EP | 1852072 A2 | 11/2007 |
| EP | 2029061 A2 | 3/2009 |
| EP | 2168507 A2 | 3/2010 |
| EP | 2303146 A1 | 4/2011 |
| EP | 2303192 A1 | 4/2011 |
| EP | 2352445 A1 | 8/2011 |
| EP | 2396741 A1 | 12/2011 |
| EP | 2398381 A1 | 12/2011 |
| EP | 2403437 A2 | 1/2012 |
| EP | 2491873 A2 | 8/2012 |
| EP | 2502582 A1 | 9/2012 |
| EP | 2709568 A1 | 3/2014 |
| FR | 2659226 A1 | 9/1991 |
| FR | 2721195 A1 | 12/1995 |
| FR | 2768916 A1 | 4/1999 |
| FR | 2979817 A1 | 3/2013 |
| GB | 2094590 A | 9/1982 |
| GB | 2197790 A | 6/1988 |
| GB | 2442441 A | 4/2008 |
| GB | 2447702 A | 9/2008 |
| GB | 2483980 A | 3/2012 |
| GB | 2486390 A | 6/2012 |
| GB | 2490220 A | 10/2012 |
| GB | 2491526 A | 12/2012 |
| JP | 59157715 A | 9/1984 |
| JP | 60231208 A | 11/1985 |
| JP | 6233790 A | 8/1994 |
| JP | 2000245758 A | 9/2000 |
| JP | 2005218861 A | 8/2005 |
| JP | 2009514612 A | 4/2009 |
| JP | 2011505080 A | 2/2011 |
| JP | 2011527885 A | 11/2011 |
| JP | 5710014 B2 | 4/2015 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| RU | 2218242 C2 | 12/2003 |
| TW | I231755 B | 5/2005 |
| TW | 201114409 A | 5/2011 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-2002026145 A1 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051233 A2 | 6/2005 |
| WO | WO-2005051239 A1 | 6/2005 |
| WO | WO-2005051240 A1 | 6/2005 |
| WO | WO-2005077039 A2 | 8/2005 |
| WO | WO-06060795 A1 | 6/2006 |
| WO | WO-2006058057 A2 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-07041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |

(56) References Cited

FOREIGN PATENT DOCUMENTS

| WO | WO-2007145937 A2 | 12/2007 |
|---|---|---|
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO 2008091358 A1 | 7/2008 |
| WO | WO-2008101090 A2 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009001109 A1 | 12/2008 |
| WO | WO-2009025783 A1 | 2/2009 |
| WO | WO-2009073781 A2 | 6/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096553 A1 | 8/2010 |
| WO | WO-2010096557 A2 | 8/2010 |
| WO | WO-2010124164 A1 | 10/2010 |
| WO | WO-2010129870 A1 | 11/2010 |
| WO | WO-2010144705 A1 | 12/2010 |
| WO | WO-2010148103 A1 | 12/2010 |
| WO | WO-2010150223 A1 | 12/2010 |
| WO | WO-2011018458 A1 | 2/2011 |
| WO | WO-2011019797 A3 | 2/2011 |
| WO | WO-2011041398 A1 | 4/2011 |
| WO | WO-2011060536 A1 | 5/2011 |
| WO | WO-2011080260 A1 | 7/2011 |
| WO | WO-2011106711 A1 | 9/2011 |
| WO | WO-2011109260 A1 | 9/2011 |
| WO | WO-2011110374 A1 | 9/2011 |
| WO | WO-2011117644 A2 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012058349 A4 | 5/2012 |
| WO | WO-2012058353 A4 | 5/2012 |
| WO | WO-2012058355 A4 | 5/2012 |
| WO | WO-2012061042 A1 | 5/2012 |
| WO | WO-2012116206 A1 | 8/2012 |
| WO | WO-2012141790 A1 | 10/2012 |
| WO | WO-2012158917 A1 | 11/2012 |
| WO | WO-2012173929 A1 | 12/2012 |
| WO | WO-2012174008 A1 | 12/2012 |
| WO | WO-2013170872 A1 | 11/2013 |
| WO | WO-2014019712 A1 | 2/2014 |
| WO | WO-2014070889 | 5/2014 |
| WO | WO-2015084831 A1 | 6/2015 |
| WO | WO-2016209585 A1 | 12/2016 |

OTHER PUBLICATIONS

"U.S. Appl. No. 14/750,325, Non Final Office Action dated Jan. 12, 2018", 16 pgs.
"International Application Serial No. PCT/US2016/035506, International Preliminary Report on Patentability dated Jan. 4, 2018", 9 pgs.
"3D-Implantatplanung and StereolithographieImplantatbohrschablonen", Stomatologie 101.3, (2004), 55-59.
"Amazing Precision. Beautiful Results. The next evolution of MAKOplasty® is here", MAKO Surgical Corp., (Feb. 2009), 6 pgs.
"Ascent Total Knee System", Biomet, Inc., (Oct. 31, 1999), 16 pgs.
"Australian Application Serial No. 2013222609, First Examiner Report dated Feb. 16, 2015", 5 pgs.
"Comprehensive® Reverse Shoulder System", Biomet Orthopedics brochure, (2009), 8 pgs.
"Comprehensive® Reverse Shoulder System Surgical Technique", Biomet Orthopedics, (2009-2012), 48 pgs.
"Comprehensive® Reverse Shoulder System Technical Design Features", Biomet Orthopedics, (2009), 3 pgs.
"Comprehensive® Shoulder System Surgical Technique", Biomet Orthopedics brochure, (2007), 1-53.
"Comprehensive® Total Shoulder System", Biomet Orthopedics brochure, (2011), 4 pgs.
"Customized Patient Instruments, Patient specific instruments for patient specific needs", DePuy Orthopaedics, Inc., (2008), 14 pgs.
"Customized Patient Instruments, Primary Cruciate Retaining Surgical Technique for use with the Sigma® Knee System Utilizing Specialist® 2 Instrumentation", DePuy Orthopaedics, Inc., (2008), 1-23.
"Discovery® Elbow System", Biomet Orthopedics, Inc., (Nov. 30, 2007), 3 pgs.
"Discovery® Elbow System Surgical Technique", Biomet Orthopedics, Inc., (Dec. 31, 2008), 1-25.
"European Application Serial No. 07809326.7, Examination Notification Art. 94(3) dated Jan. 22, 2015", 6 pgs.
"European Application Serial No. 07809326.7, Extended European Search Report dated Nov. 15, 2011", 6 pgs.
"European Application Serial No. 09731923.0, Examination Notification Art. 94(3) dated Feb. 10, 2015", 7 pgs.
"European Application Serial No. 10705064.3, Examination Notification Art. 94(3) dated Feb. 4, 2015", 6 pgs.
"European Application Serial No. 12724475.4, Examination Notification Art. 94(3) dated Nov. 24, 2014", 7 pgs.
"Great Britain Application Serial No. 1116054.6, Search Report dated Dec. 21, 2011", 4 pgs.
"Hipsextant Instructions of Use", Surgical Planning Associates, Inc., (2011), 19 pgs.
"International Application Serial No. PCT/EP2010/061630, International Search Report dated Nov. 30, 2010", 3 pgs.
"International Application Serial No. PCT/US2007/013223, International Preliminary Report on Patentability dated Dec. 24, 2008", 5 pgs.
"International Application Serial No. PCT/US2007/013223, International Search Report dated Nov. 26, 2007", 3 pgs.
"International Application Serial No. PCT/US2007/013223, Written Opinion dated Nov. 26, 2007", 4 pgs.
"International Application Serial No. PCT/US2009/039507, International Preliminary Report on Patentability dated Oct, 28, 2010", 9 pgs.
"International Application Serial No. PCT/US2009/039507, International Search Report dated Jul. 14, 2009", 6 pgs.
"International Application Serial No. PCT/US2009/039507, Written Opinion dated Jul. 14, 2009", 7 pgs.
"International Application Serial No. PCT/US2009/039578, International Preliminary Report on Patentability dated Oct. 28, 2010", 9 pgs.
"International Application Serial No. PCT/US2009/039578, International Search Report dated Jul. 31, 2009", 6 pgs.
"International Application Serial No. PCT/US2009/039578, Written Opinion dated Jul. 31, 2009", 7 pgs.
"International Application Serial No. PCT/US2009/056670, International Preliminary Report on Patentability dated Mar. 31, 2011", 12 pgs.
"International Application Serial No. PCT/US2009/056670, International Search Report dated Mar. 2, 2010", 7 pgs.
"International Application Serial No. PCT/US2009/056670, Invitation to Pay Additional Fees and Partial Search Report dated Nov. 26, 2009".
"International Application Serial No. PCT/US2009/056670, Written Opinion dated Mar. 2, 2010", 10 pgs.
"International Application Serial No. PCT/US2010/024073, International Preliminary Report on Patentability dated Aug. 25, 2011", 8 pgs.
"International Application Serial No. PCT/US2010/024073, International Search Report dated Jun. 4, 2010", 4 pgs.
"International Application Serial No. PCT/US2010/024073, Written Opinion dated Jun. 4, 2010", 6 pgs.
"International Application Serial No. PCT/US2010/024579, International Preliminary Report on Patentability dated Sep. 1, 2011", 7 pgs.
"International Application Serial No. PCT/US2010/024579, International Search Report dated Apr. 22, 2010", 3 pgs.

(56) References Cited

OTHER PUBLICATIONS

"International Application Serial No. PCT/US2010/024579, Written Opinion dated Apr. 22, 2010", 5 pgs.
"International Application Serial No. PCT/US2010/024584, International Preliminary Report on Patentability dated Sep. 1, 2011", 8 pgs.
"International Application Serial No. PCT/US2010/024584, International Search Report dated Aug. 9, 2010", 6 pgs.
"International Application Serial No. PCT/US2010/024584, Written Opinion dated Aug. 19, 2010", 6 pgs.
"International Application Serial No. PCT/US2010/038177, International Preliminary Report on Patentability dated Dec. 22, 2011", 10 pgs.
"International Application Serial No. PCT/US2010/038177, International Search Report dated Aug. 24, 2010", 4 pgs.
"International Application Serial No. PCT/US2010/038177, Written Opinion dated Aug. 24, 2010", 8 pgs.
"International Application Serial No. PCT/US2010/038845, International Preliminary Report on Patentability dated Jan. 5, 2012", 9 pgs.
"International Application Serial No. PCT/US2010/038845, International Search Report dated Oct. 5, 2010", 4 pgs.
"International Application Serial No. PCT/US2010/038845, Written Opinion dated Oct. 5, 2010", 7 pgs.
"International Application Serial No. PCT/US2010/050701, International Preliminary Report on Patentability dated Apr. 12, 2012", 10 pgs.
"International Application Serial No. PCT/US2010/050701, International Search Report dated Dec. 7, 2010", 6 pgs.
"International Application Serial No. PCT/US2010/050701, Written Opinion dated Dec. 7, 2010", 8 pgs.
"International Application Serial No. PCT/US2011/026333, International Preliminary Report on Patentability dated Sep. 7, 2012", 10 pgs.
"International Application Serial No. PCT/US2011/026333, International Search Report dated Aug. 9, 2011", 6 pgs.
"International Application Serial No. PCT/US2011/026333, Invitation to Pay Additional Fees dated May 3, 2011".
"International Application Serial No. PCT/US2011/026333, Written Opinion dated Aug. 9, 2011", 8 pgs.
"International Application Serial No. PCT/US2011/026412, International Search Report dated May 9, 2011", 5 pgs.
"International Application Serial No. PCT/US2011/026412, Written Opinion dated May 9, 2011", 6 pgs.
"International Application Serial No. PCT/US2011/057300, International Search Report dated Mar. 5, 2012", 7 pgs.
"International Application Serial No. PCT/US2011/057300, Written Opinion dated Mar. 5, 2012", 9 pgs.
"International Application Serial No. PCT/US2012/026356, International Preliminary Report on Patentability dated Sep. 6, 2013", 8 pgs.
"International Application Serial No. PCT/US2012/026356, International Search Report dated May 8, 2012", 5 pgs.
"International Application Serial No. PCT/US2012/026356, Written Opinion dated May 8, 2012", 6 pgs.
"International Application Serial No. PCT/US2012/0 8351, International Preliminary Report on Patentability dated Nov. 28, 2013", 9 pgs.
"International Application Serial No. PCT/US2012/038351, Written Opinion dated Jul. 6, 2012", 8 pgs.
"International Application Serial No. PCT/US2012/041893, International Search Report dated Oct. 23, 2012", 5 pgs.
"International Application Serial No. PCT/US2012/042081, International Preliminary Report on Patentability dated Jan. 3, 2014", 7 pgs.
"International Application Serial No. PCT/US2012/042081, Written Opinion dated Sep. 5, 2012", 6 pgs.
"International Application Serial No. PCT/US2012/052853, International Preliminary Report on Patentability dated Mar. 13, 2014", 14 pgs.
"International Application Serial No. PCT/US2012/052853, International Search Report dated Nov. 15, 2012", 6 pgs.
"International Application Serial No. PCT/US2012/052853, Written Opinion dated Nov. 15, 2012", 12 pgs.
"International Application Serial No. PCT/US2012/059189, International Preliminary Report on Patentability dated Apr. 24, 2014", 10 pgs.
"International Application Serial No. PCT/US2012/059189, International Search Report dated Dec. 18, 2012", 6 pgs.
"International Application Serial No. PCT/US2012/059189, Written Opinion dated Dec. 18, 2012", 9 pgs.
"International Application Serial No. PCT/US2012/060842, International Preliminary Report on Patentability dated May 8, 2014", 7 pgs.
"International Application Serial No. PCT/US2012/060842, International Search Report dated Feb. 6, 2013", 4 pgs.
"International Application Serial No. PCT/US2012/060842, Written Opinion dated Feb. 6, 2013", 5 pgs.
"International Application Serial No. PCT/US2012/060848, International Preliminary Report on Patentability dated May 8, 2014", 11 pgs.
"International Application Serial No. PCT/US2012/060848, Invitation to Pay Additional Fees dated Feb. 6, 2013".
"International Application Serial No. PCT/US2012/060848, Written Opinion dated Apr. 12, 2013", 9 pgs.
"International Application Serial No. PCT/US2012/060853, International Preliminary Report on Patentability dated May 8, 2014", 11 pgs.
"International Application Serial No. PCT/US2012/060853, Invitation to Pay Additional Fees dated Feb. 7, 2013", 4 pgs.
"International Application Serial No. PCT/US2012/060853, Written Opinion dated Apr. 9, 2013", 9 pgs.
"International Application Serial No. PCT/US2012/060854, International Preliminary Report on Patentability dated May 8, 2014", 8 pgs.
"International Application Serial No. PCT/US2012/060854, International Search Report dated Feb. 6, 2013", 4 pgs.
"International Application Serial No. PCT/US2012/060854, Written Opinion dated Feb. 6, 2013", 6 pgs.
"International Application Serial No. PCT/US2013/026875, International Preliminary Report on Patentability dated Sep. 4, 2014", 9 pgs.
"International Application Serial No. PCT/US2013/026875, International Search Report dated Jun. 7, 2013", 5 pgs.
"International Application Serial No. PCT/US2013/026875, Written Opinion dated Jun. 7, 2013", 8 pgs.
"International Application Serial No. PCT/US2013/057097, International Preliminary Report on Patentability dated Mar. 12, 2015", 10 pgs.
"International Application Serial No. PCT/US2013/057097, International Search Report dated Oct. 14, 2013", 6 pgs.
"International Application Serial No. PCT/US2013/057097, Written Opinion dated Oct. 14, 2013", 9 pgs.
"International Application Serial No. PCT/US2013/067505, International Preliminary Report on Patentability dated May 14, 2015", 13 pgs.
"International Application Serial No. PCT/US2013/067505, International Search Report dated Apr. 14, 2014", 5 pgs.
"International Application Serial No. PCT/US2013/067505, Invitation to Pay Additional Fees dated Feb. 6, 2014", 6 pgs.
"International Application Serial No. PCT/US2013/067505, Written Opinion dated Apr. 14, 2014", 11 pgs.
"International Application Serial No. PCT/US2013/074288, International Search Report dated May 23, 2014", 7 pgs.
"International Application Serial No. PCT/US2013/074288, Written Opinion dated May 23, 2014", 11 pgs.
"International Application Serial No. PCT/US2014/022000, International Search Report dated Jun. 24, 2014", 3 pgs.
"International Application Serial No. PCT/US2014/022000, Written Opinion dated Jun. 24, 2014", 5 pgs.
"International Application Serial No. PCT/US2014/023655, International Search Report dated Jul. 10, 2014", 4 pgs.

(56) References Cited

OTHER PUBLICATIONS

"International Application Serial No. PCT/US2014/023655, Written Opinion dated Jul. 10 2014", 6 pgs.
"International Application Serial No. PCT/US2014/068131, International Search Report dated May 8, 2015", 5 pgs.
"International Application Serial No. PCT/US2014/068131, Written Opinion dated May 8, 2015", 9 pgs.
"International Application Serial No. PCT/US2016/035506, International Search Report dated Sep. 6, 2016", 4 pgs.
"International Application Serial No. PCT/US2016/035506, Written Opinion dated Sep. 6, 2016", 7 pgs.
"Is Subchondroplasty® Right for Me?", [Online] retrieved from the internet: <http://www.subchondroplast}'. . . com/about subchondroplast}'./subchondroplasty right for >, (Jul. 1, 2013), 1 pg.
"Japanese Application Serial No. 2014511538, Office Action dated Apr. 7, 2015", (W/ English Translation), 8 pgs.
"Knee tensor combined with laser femoral head locator", Research Disclosure, No. 507, (Jul. 2006), 903.
"Method for constructing an allograft sleeve", Research Disclosure, No. 476, (Dec. 2003), 1294.
"OSS™ Orthopaedic Salvage System, Femoral/Tibial Augmentation", Biomet Orthopedics, Inc.,, (Mar. 31, 2004), 1-8.
"Oxford® Partial Knee", Biomet, (Feb. 2011), 8 pgs.
"Oxford® Partial Knee Microplasty® Instrumentation Surgical Technique", Biomet, (May 2011), 1-54.
"Patient Matched PMI Implants, C.A.M.R.A. 3-D Imaging", Brochure, Biomet, Inc., Form Y-BMI-191/013191, (1991), 6 pgs.
"Regenerex® Tibial Cone Augment, Surgical Technique Addendum to the Vanguard® SSK Revision System", brochure. Biomet® Orthopedics., (Mar. 31, 2010), 1-8.
"Signature™ Hip Technology Personalized Patient Care brochure", Biomet® Orthopedics., (2013), 8 pgs.
"Signature™ Personalized Patient Care", Surgical Technique Acetabular Guide System brochure, Biomet® Orthopedics, (2013), 1-13.
"Signature™ Personalized Patient Care, Surgical Technique Addendum to the Vanguard Knee System", Biomet® Orthopedics Brochure, (May 15, 2009), 1-8.
"Subchondroplasty", [Online] retrieved from the internet: <http://www.subchondroplasty.com/>, (Jul. 1, 2013), 1 pg.
"The Oxford® Partial Knee Surgical Technique", Biomet, (Feb. 2010), 1-38.
"TruMatch™ Personalized knee replacement solutions", SIGMA® DePuy Orthopaedics, Inc, tri-fold brochure, (2009), 2 pgs.
"Vanguard® PFR Partial Knee Patellofemoral Replacement System", Surgical Technique, Biomet Orthopaedics,, (Aug. 31, 2010), 1-25.
"What is Subchondroplasty", [Online]. Retrieved from the Internet: <http://www.subchondroplasty.com/about subchondroplasty/what is subchondroplasty.>, (Jul. 1, 2013), 2 pgs.
"Zimmer® UniSpacer® Knee System", Zimmer, Inc., (2005), 4 pgs.
Birnbaum, Klaus M. D, "Computer-Assisted Orthopedic Surgery With Individual Templates and Comparison to Conventional Method", SPINE vol. 26, No. 4, Lippincott Williams & Wilkins, Inc., (2001), 365-370.
Botha, Charl P, "Technical Report: DeVIDE—The Delft Visualisation and Image processing Development Environment", (May 31, 2006), 1-49.
Cohen, Zohara A, et al., "Knee cartilage topography, thickness, and contact areas from MRI: in-vitro calibration and in-vivo measurements", Journal of the OsteoArthritis Research Society International. Osteoarthritis and Cartilage, vol. 7; No. 1, (1999), 95-109.
"U.S. Appl. No. 14/750,325, Preliminary Amendment filed Sep. 10, 2015", 10 pgs.
"U.S. Appl. No. 14/750,325, Notice of Allowance dated Oct. 29, 2018", 9 pgs.
"U.S. Appl. No. 14/750,325, Response filed Oct. 5, 2018 to Final Office Action dated Aug. 8, 2018", 12 pgs.

"European Application Serial No. 16732055.5, Response filed Sep. 13, 2018 to Office Action dated Mar. 3, 2018", 84 pgs.
"Ascent Total Knee System", Biornet, Inc., (Oct. 31, 1999), 16 pgs.
"International Application Serial No. PCT/US2009/056670, International Preliminary Report on Patentability dated Mar. 21, 2011", 12 pgs.
"International Application Serial No. PCT/US2010/024584, International Search Report dated Aug. 19, 2010", 6 pgs.
"International Application Serial No. PCT/US2012/038351, International Preliminary Report on Patentability dated Nov. 28, 2013", 9 pgs.
"International Application Serial No. PCT/US2013/026875, International Search Report mailed Jun. 7, 2013", 5 pgs.
"Is Subchondroplasty® Right for Me?", [Online] retrieved from the internet: <http://www.subchondroplast}'. . . com/about subchondroplast}'./is subchondroplasty right for >, (Jul. 1, 2013), 1 pg.
Deakon, "Posterior Cruciate Ligament Reconstruction Technique Using the Modular ACL/PCL Guide Rationale and Surgical Technique", Arthrotek®, a Biomet Company, (2003), 6 pgs.
Eckhoff, Donald G, et al., "Three-Dimensional Mechanics, Kinematics, and Morphology of the Knee Viewed in Virtual Reality", The Journal of Bone & Joint Surgery, vol. 81, (Dec. 4, 2005), 71-80.
Farr, J, et al., "Anteromedial Tibial Tubercle Osteotomy (Fulkerson Osteotomy)", Re-print from V. Sanchis-Alfonso (ed), Anterior Knee Pain and patellar Instability, DOI: 10.1007/978-0-85729-507-1_40, © Springer-Verlag London Limited, (2011), 9 pgs.
Farr, J, et al., "Surgical Technique for Anteromedialization of the Tibial Tubercle with the Tracker™ AMZ Guide System", Sports Medicine and Arthroscopy Review, vol. 2, No. 3, (1994), 12 pgs.
Fortin, Thomas, et al., "Precise Dental Implant Placement in Bone Using Surgical Guides in Conjunction with Medical Imaging Techniques", Journal of Oral Implantology, Clinical, vol. 26, No. 4, (2000), 300-303.
Friedman, R J, et al., "The Use of Computerized Tomography in The Measurement of Glenoid Version", Journal of Bone & Joint Surgery Am. (JBJS) 1992;74, (Aug. 1992), 1032-1037.
Haaker, R G, et al., "Minimal-invasive navigiert implantierte unikondylare Knieendoprothese", Orthopade 2006 35: Spinger Medizin Verlag, (Sep. 13, 2006), 1073-1079.
Hafez, M A, et al., "Computer-assisted Total Knee Arthroplasty Using Patient-specific Templating", Clinical Orthopaedics and Related Research, No. 444 Lippincott Williams & Wilkins, (2006), 184-192.
Hazan, Eric J, "Computer-Assisted Orthopaedic Surgery, A New Paradigm", Techniques in Orthopaedics® vol. 18, No. 2,, (2003), 221-229.
Hutmacher, Dietmar W, "Scaffolds in tissue engineering bone and cartilage", Biomaterials, 21(24), (2000), 2529-2543.
Kaus, Michael R, "Automated Segmentation of MR Images of Brain Tumors", Radiology, vol. 218, No. 2,, (2001), 586-591.
Kelly, Todd C, "Role of Navigation in Total Hip Arthroplasty", The Journal of Bone & Joint Surgery(2009) vol. 91-A, Supplement 1, (2009), 153-8.
Klein, M, "Robot assisted insertion of craniofacial implants—clinical experience", CARS 2001, Elsevier Science B.V., (2001), 133-138.
Lombardi, Adolph, et al., "Patient-Specific Approach in Total Knee Arthroplasty", Knee Orthopedics, ORTHOSuperSite, [Online]. Retrieved from the Internet: <http://www.orthosupersite.com/view.aspx?rid=31419,>, (Sep. 1, 2008), 5 pgs.
Lynch, John A, et al., "Cartilage segmentation of 3D MRI scans of the osteoarthritic knee combining user knowledge and active contours", Medical Imaging 2000: Image Processing SPIE vol. 3979, (2000), 925-935.
Murphy, S B, et al., "The Hip Sextant: Navigation of Acetabular Component Orientation Using a Mechanical Instrument", (2009), 1 pg.
Nicholls, Paul M. D, "Trauma Grand Rounds PMI (Patient-Matched Implants)", Biomet Orthopedics, Inc., (Feb. 29, 2000), 1 pg.
Overhoff, H M, et al., "Total Knee Arthroplasty: Coordinate System Definition and Planning based on 3-D Ultrasound Image Volumes", CARS 2001, Elsevier Science B.V., (2001), 283-288.

(56) References Cited

OTHER PUBLICATIONS

Portheine, F, "CT-basierte Planung und DISOS-Schablonennavigation in der Kniegelenkendoprothetik", Navigation und Robotic in der Gelenk—und Wirbelsaulenchiruqie, Kapitel 32, Springer Verlag, (2003), 262-269.

Portheine, F, et al., "Entwicklung eines klinischen Demonstrators fur die computerunterstutzte Orthopadische Chirurgie mit CT-Bildbasierten Individualschablonen, Bildverarbeitung fur die Medizin", English version: FIP ID 752773, (1998), 5 pgs.

Portheine, K, "Development of a clinical demonstrator for computer assisted orthopedic surgery with CT-image based individual templates", Computer Assisted Radiology and Surgery Elsevier Science B.V., English Version of FIP ID 752770, (1997), 944-949.

Radermacher, K, et al., "Computer Integrated Orthopaedic Surgery: Connection of Planning and Execution in Surgical Intervention", Computer-integrated surgery: technology and clinical applications, (1996), 451-463.

Radermacher, K, et al., "CT Image-Based Planning and Execution of Interventions in Orthopedic Surgery Using Individual Templates, Experimental Results and Aspects of Clinical Applications", Computer Assisted Orthopedic Surgery (CAOS), Hogrefe & Huber Publishers, (1995), 42-52.

Radermacher, K, et al., "Image Guided Orthopedic Surgery Using Individual Templates", Springer Berlin/Heidelberg, CVRMed-MRCAS'97, vol. 1205, (1997), 606-615.

Radermacher, K, et al., "Technique for Better Execution of CT Scan Planned Orthopedic Surgery on Bone Structures", British Library— "The world's knowledge" 2nd Congress of ISCAS Conference, (Jun. 1995), 933-938.

Radermacher, Klaus, et al., "Computer Assisted Orthopaedic Surgery with Image Based Individual Templates", Clincal Orthopaedics and Related Research No. 354, Lippincott Williams & Wilkins, (Sep. 1998), 28-38.

Sharp, Michael S, "Patient-Specific, Resurfacing Bi-Compartmental Arthuroplasty Futuretech", Orthopaedic Product News, (Apr. 2008), 12-15.

Sisto, Domenick J, et al., "Custom Patellofemoral Arthroplasty of the Knee Surgical Technique", Journal of Bone and Joint Surgery, vol. 89-A, (2006), 214-225.

Slamin, John, et al., "Do You Have This Implant in My Size?", MDT Medical Design Technology, [Online]. Retrieved from the Internet: <http://www.mdtmag.com/scripts/ShowPR.asp?PUBCODE=046&ACCT=0007796&ISSUE . . . >, (Jul. 31, 2008), 3 pgs.

Steinwachs, Matthias Reinhard, "Cartilage Repair—Autologous Chondrocyte Transplantation and Autologous Matrix-induced Chondrogenesis", European Musculoskeletal Review, (2006), 65-68.

Subburaj, K, et al., "Automated 3D Geometric Reasoning in Computer Assisted Joint Reconstructive Surgery", IEEE International Conference on Automation Science and Engineering, (2009), 367-372.

Thoma, W, et al., "Endoprothetischen Versorgung des Kniegelenks auf der Basis eines 3D-computertomographischen Subtraktionsverfahrens", Topic: Computer-aided orthopedic surgery. Orthopedist 2000 29: Springer Verlag W/ Original German Document, (2000), 641-644.

"U.S. Appl. No. 16/257,967, Preliminary Amendment filed Mar. 11, 2019", 7 pgs.

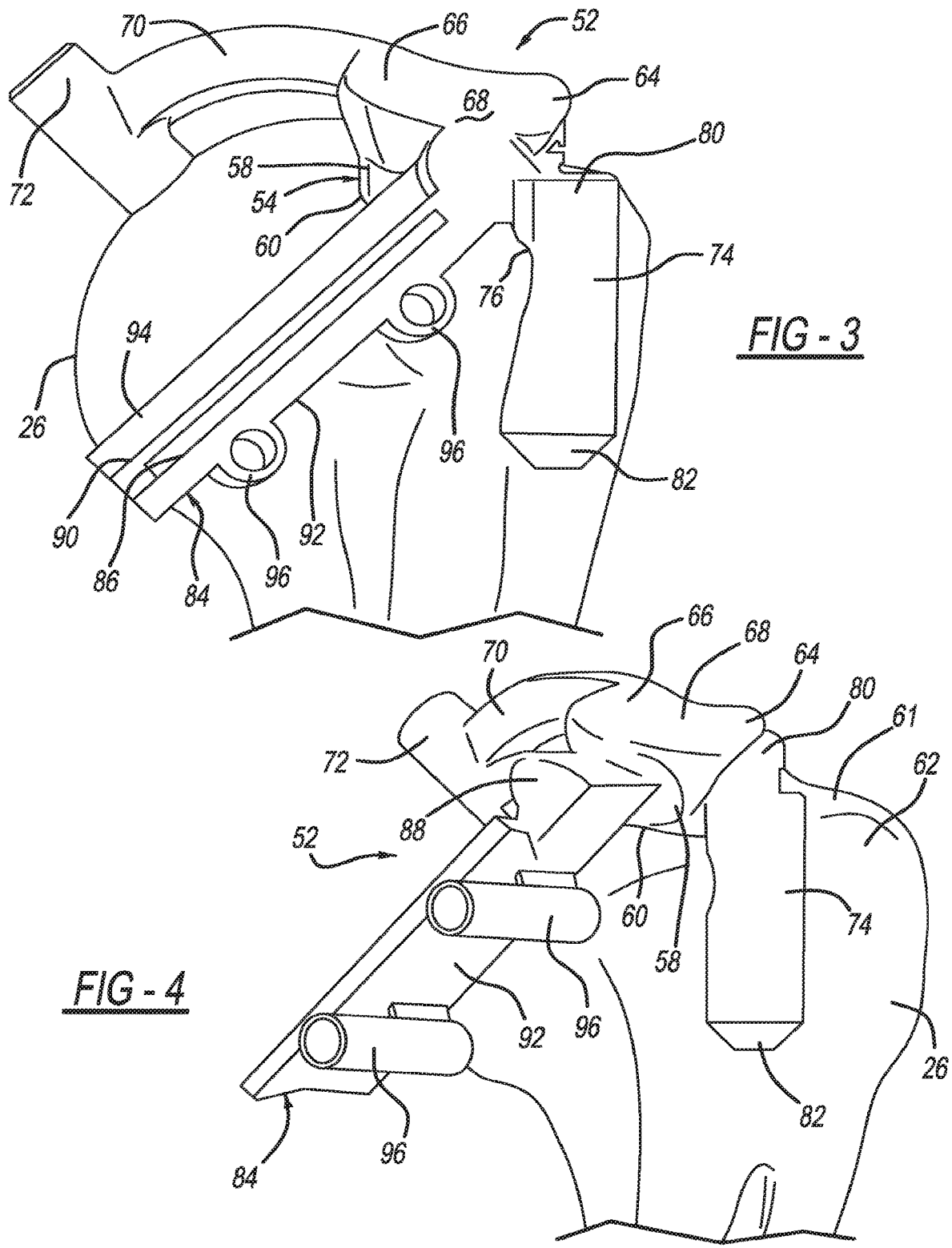

PATIENT-SPECIFIC HUMERAL GUIDE DESIGNS

CLAIM OF PRIORITY

This patent application is a continuation-in-part of Kehres et al, U.S. patent application Ser. No. 14/750,325, entitled "PATIENT-SPECIFIC HUMERAL GUIDE DESIGNS," filed on Jun. 25, 2015, the benefit of priority of which is claimed hereby, and which is incorporated by reference herein in its entirety.

FIELD

The present disclosure relates to humeral cut guide members.

BACKGROUND

This section provides background information related to the present disclosure which is not necessarily prior art.

During shoulder arthroplasty, the humeral bone may require resurfacing or resecting for receipt of a shoulder implant. Prior to surgery, it is common for the surgeon to take various images via X-ray, CT, ultrasound, MRI, or PET of the surgical area including the humeral bone. Based on these images, the surgeon can determine the best course of action for resurfacing or resecting the humeral bone, as well as determine whether the primary procedure for shoulder repair is an anatomical or reverse arthroplasty. During the surgery, however, it is not uncommon for the surgeon to determine that the preselected courses of action are not suitable for the patient. If the course of action changes during surgery, new instruments may be required to properly complete the resurfacing or resecting of the humeral bone before completing the arthroplasty procedure.

SUMMARY

This section provides a general summary of the disclosure, and is not a comprehensive disclosure of its full scope or all of its features.

The present disclosure provides a humeral cut guide system for a humeral head comprises: a bone-engagement member including a first patient-specific bone-engagement surface that is complementary and made to substantially mate and nest in only one position on a specific patient's humeral head; a registration member connected to the bone-engagement member including a second patient-specific bone engagement surface that is sized and made to substantially mate and nest in only one position with the specific patient's bicipital groove; a first protrusion extending from the registration member and having a first surgeon-engaging surface for manipulation by a surgeon; and a cut guide plate connected to and extending away from the registration member such that, upon the bone-engagement member mating and nesting with the specific patient's humeral head, the cut guide plate is spaced apart from the humeral head, wherein the cut guide plate defines an elongate slot.

The present disclosure also provides a humeral cut guide system for a humeral head comprising: a bone-engagement member including a first patient-specific bone-engagement surface that is complementary and made to substantially mate and nest in only one position on a specific patient's humeral head; a registration member connected to the bone-engagement member including a second patient-specific bone engagement surface that is sized and made to substantially mate an nest in only one position with the specific patient's bicipital groove; an elongate member extending from the registration member; and a cut guide plate having a connection portion with a socket configured to receive the elongate member such that a position of the cut guide plate relative to the specific patient's humeral head is selectively adjustable along the elongate member in an infinite number of positions.

The present disclosure also provides a method of resecting or resurfacing a humeral head using a humeral cut guide comprising: positioning a bone-engagement member along a humeral head surface of a humeral bone; positioning a registration member along a bicipital groove surface of a humeral bone; squeezing the registration member and the bone-engagement member to ensure seating of the humeral cut guide; sliding a cut guide plate along an elongate member extending from the humeral cut guide to engage the humeral head surface of the humeral bone; and resecting or resurfacing the humeral head using a cutting device engaged with the cut guide plate.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 3 is a perspective environmental view of a humeral cut guide member according to a first embodiment of the present disclosure;

FIG. 4 is another perspective environmental view of the humeral cut guide member according to the first embodiment of the present disclosure;

Corresponding reference numerals indicate corresponding parts throughout the several views of the drawings.

DETAILED DESCRIPTION

Figure 1:
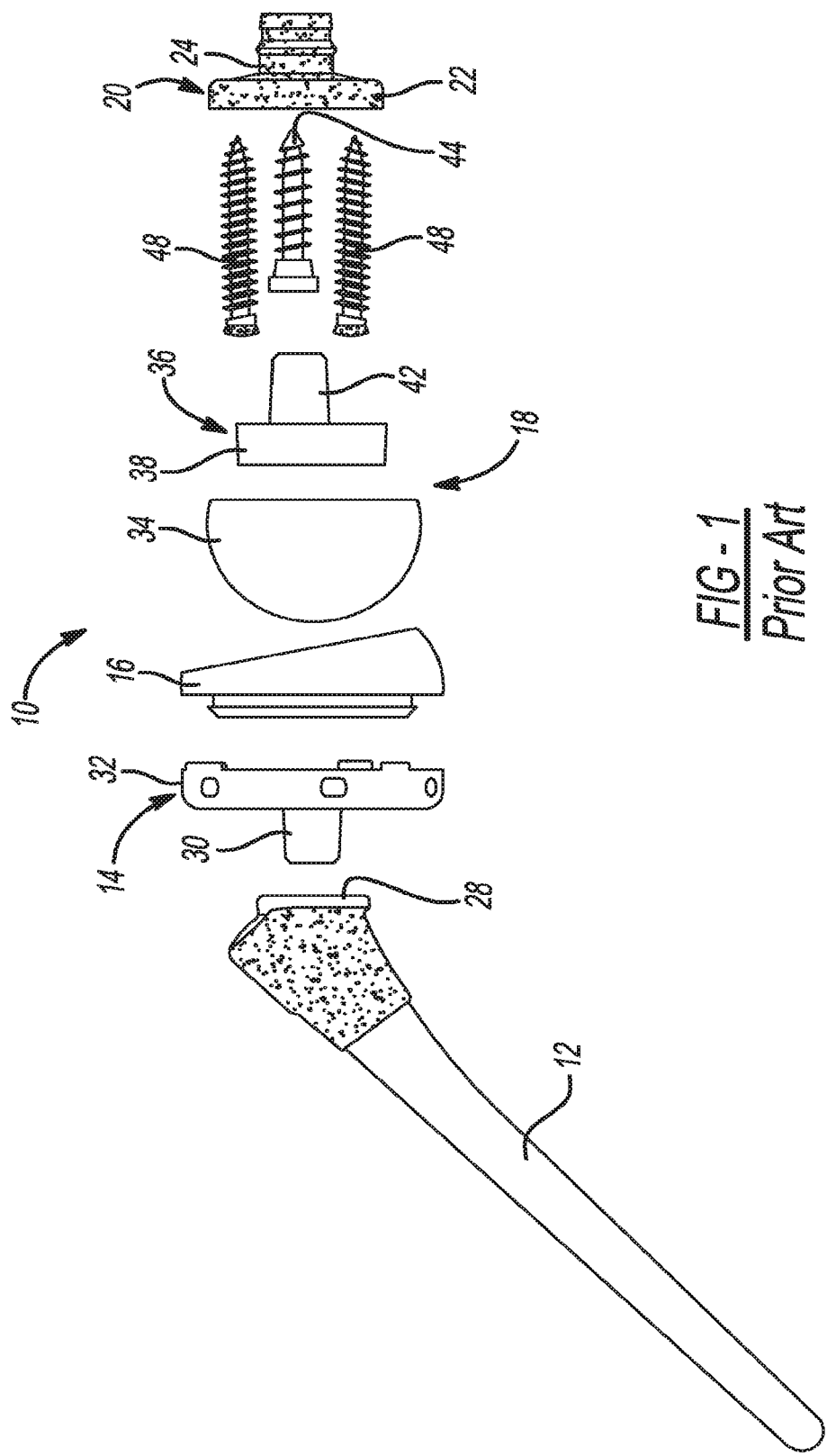
FIG. 1 is an exploded view of a prior art implant for reverse shoulder arthroplasty.

Example embodiments will now be described more fully with reference to the accompanying drawings.

The present disclosure generally provide patient-specific surgical instruments that include, for example, alignment guides, drill guides, and other tools for use in shoulder joint replacement, shoulder resurfacing procedures and other procedures related to the shoulder joint or the various bones of the shoulder joint, including the humeral head. The present disclosure can be applied to anatomic shoulder replacement and reverse shoulder replacement. The patient-specific instruments can be used either with conventional implant components or with patient-specific implant components and/or bone grafts that are prepared using computer-assisted image methods according to the present disclosure. Computer modeling for obtaining three-dimensional images of the patient's anatomy using medical scans of the patient's anatomy (such as MRI, CT, ultrasound, X-rays, PET, etc.), the patient-specific prosthesis components and the patient-specific guides, templates and other instruments, can be prepared using various commercially available CAD programs and/or software available, for example, by Object Research Systems or ORS, Montreal, Canada.

The patient-specific instruments and any associated patient-specific implants and bone grafts can be generally designed and manufactured based on computer modeling of the patient's 3-D anatomic image generated from medical image scans including, for example, X-rays, MRI, CT, PET, ultrasound or other medical scans. The patient-specific instruments can have a three-dimensional engagement surface that is complementary and made to substantially mate and match in only one position (i.e., as a substantially negative or mirror or inverse surface) with a three-dimensional bone surface with or without associated soft tissues, which is reconstructed as a 3-D image via the aforementioned CAD or software. Very small irregularities need not be incorporated in the three-dimensional engagement surface. The patient-specific instruments can include custom-made guiding formations, such as, for example, guiding bores or cannulated guiding posts or cannulated guiding extensions or receptacles that can be used for supporting or guiding other instruments, such as drill guides, reamers, cutters, cutting guides and cutting blocks or for inserting guiding pins, K-wire, or other fasteners according to a surgeon-approved pre-operative plan.

In various embodiments, the patient-specific instruments of the present disclosure can also include one or more patient-specific guide members for receiving and guiding a tool, such as a drill or saw at corresponding patient-specific insertion points and orientations relative to a selected anatomic or reverse axis for the specific patient. The patient-specific instruments can include guiding or orientation formations and features for guiding the implantation of patient-specific or off-the-shelf implants associated with the surgical procedure. The geometry, shape and orientation of the various features of the patient-specific instruments, as well as various patient-specific implants and bone grafts, if used, can be determined during the pre-operative planning stage of the procedure in connection with the computer-assisted modeling of the patient's anatomy. During the pre-operative planning stage, patient-specific instruments, custom, semi-custom or non-custom implants and other non-custom tools, can be selected and the patient-specific components can be manufactured for a specific-patient with input from a surgeon or other professional associated with the surgical procedure.

In the following discussion, the terms "patient-specific", "custom-made" or "customized" are defined to apply to components, including tools, implants, portions or combinations thereof, which include certain geometric features, including surfaces, curves, or other lines, and which are made to closely conform substantially as mirror-images or negatives or complementary surfaces of corresponding geometric features or anatomic landmarks of a patient's anatomy obtained or gathered during a pre-operative planning stage based on 3-D computer images of the corresponding anatomy reconstructed from image scans of the patient by computer imaging methods. Further, patient-specific guiding features, such as, guiding apertures, guiding slots, guiding members or other holes or openings that are included in alignment guides, drill guides, cutting guides, rasps or other instruments or in implants are defined as features that are made to have positions, orientations, dimensions, shapes and/or define cutting planes and axes specific to the particular patient's anatomy including various anatomic or mechanical axes based on the computer-assisted pre-operative plan associated with the patient.

The patient-specific guide members can be configured to mate in alignment with natural anatomic landmarks by orienting and placing the corresponding alignment guide intra-operatively on top of the bone to mate with corresponding landmarks. The anatomic landmarks function as passive fiducial identifiers or fiducial markers for positioning of the various alignment guide members, drill guides or other patient-specific instruments.

The various patient-specific alignment guide members can be made of any biocompatible material, including, polymer, ceramic, metal or combinations thereof. The patient-specific alignment guide members can be disposable and can be combined or used with reusable and non-patient-specific cutting and guiding components.

More specifically, the present disclosure provides various embodiments of patient-specific humeral cut guide members for anatomic and reverse arthroplasty. The humeral cut guides of the present disclosure can have patient-specific engagement surfaces that reference various portions of the shoulder joint and include tubular drill guides, guiding bores or sleeves or other guiding formations that can accurately position guide pins for later humeral preparation and implantation procedures and for alignment purposes, including implant position control, implant version control, implant inclination control for both anatomic and reverse arthroplasty.

In the following, when a portion of a humeral guide member is described as "referencing" a portion of the anatomy, it will be understood that the referencing portion of the humeral guide member is a patient-specific portion that mirrors or is a negative of the corresponding referenced anatomic portion.

In some embodiments the humeral guide member can have built-in holes, openings or windows that allow the surgeon to mark the humeral bone or a model of the humeral bone with a marking pen, burr, scalpel, or any other device that can create markings to be used as landmarks on or in the humeral bone or humeral model. These landmarks can be used for the orientation of a secondary guide.

Figure 2:
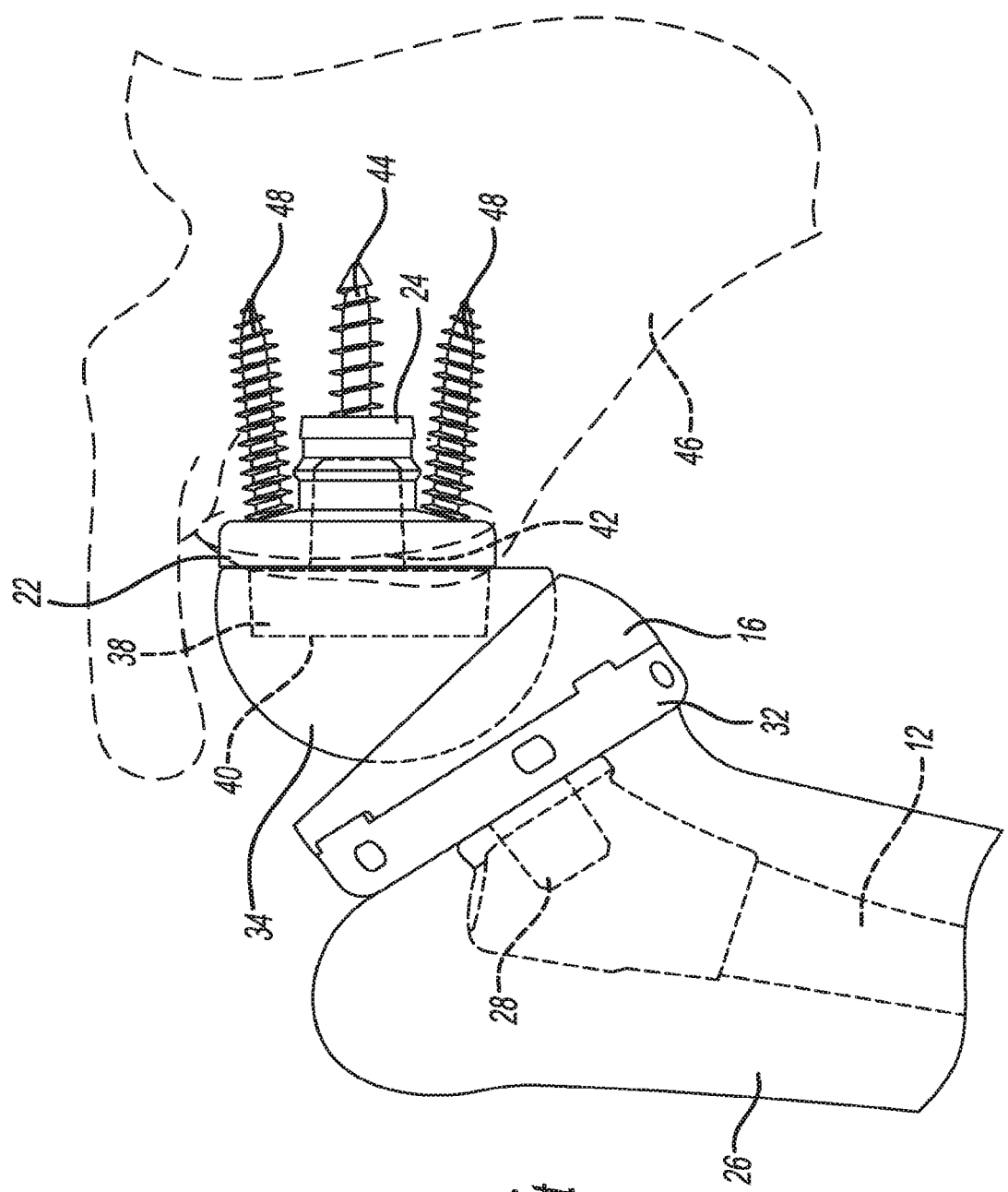
FIG. 2 is an environmental view of the prior art implant of FIG. 1.

Referring to FIGS. 1 and 2, a prior art reverse shoulder implant 10 is illustrated. The reverse shoulder implant 10 includes a humeral stem 12, a humeral tray 14, a humeral bearing 16, a glenosphere 18 and a baseplate 20 having a plate portion 22 and a central boss 24. The humeral stem 12 is implanted in the humeral bone 26 and has a proximal end 28 coupled via a Morse taper connection to a male taper 30 extending from a plate 32 of the humeral tray 14. The glenosphere 18 can be modular and include a head 34 articulating with the bearing 16 and an offset double-taper component 36. The double-taper component 36 has a first tapered portion 38 coupled to a corresponding tapered opening 40 of the head 34 and a second tapered portion 42 coupled to the central boss 24 of the glenoid baseplate 20. A central screw 44 passes through the baseplate 20 into the glenoid face 46 of the patient's scapula. Peripheral screws 48 are used to lock the baseplate 20 in the glenoid face 46.

As best illustrated in FIG. 2, humeral bone 26 includes a planar surface 50 for abutment with plate 32 of humeral tray 14. To provide planar surface 50, humeral bone 26 is cut using a tool such as a bone saw (not shown). To properly orient the saw at the correct angle relative to humeral bone 26, the present disclosure provides a humeral cut guide system 52.

Figure 5:
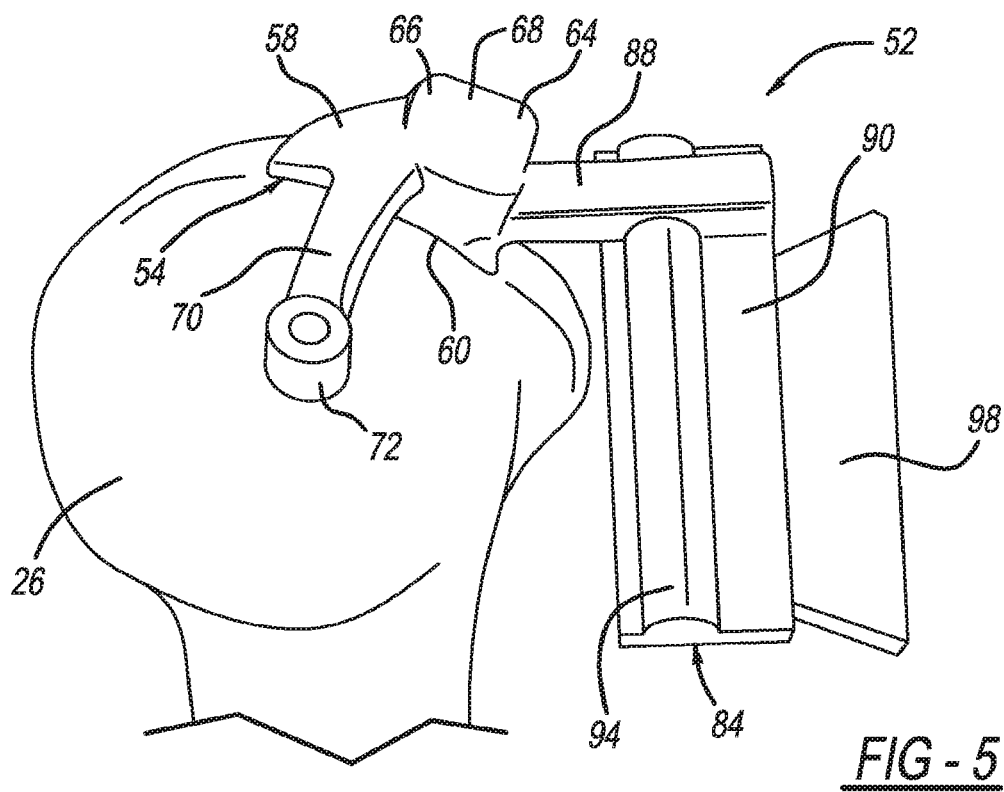
FIG. 5 is another perspective environmental view of the humeral cut guide member according to the first embodiment of the present disclosure.

Referring to FIGS. 3-5, an exemplary humeral cut guide system 52 according to an aspect of the present disclosure is illustrated. Humeral cut guide system 52 includes a patient-specific humeral cut guide member 54. Humeral cut guide member 54 is configured to be patient-specific such that humeral cut guide member 54 mates with and nests in only one position on humeral bone 26. In this regard, humeral cut guide member 54 includes a bone-engagement member 58 having a bone-engagement surface 60 that is complementary and made to substantially mate and nest in only one position (i.e., as a substantially negative or mirror or inverse surface) with a three-dimensional bone surface 61 of humeral bone 26 with or without associated soft tissues, which is reconstructed as a 3-D image via the aforementioned CAD or software.

As best illustrated in FIG. 3, bone-engagement member 58 and bone-engagement surface 60 are each pie-shaped and specifically designed to mate and nest on a proximal portion of the lesser tuberosity 62 of humeral bone 26. An opposing surface 64 of bone-engagement member 58 defines a protrusion 66 that provides a curved contact surface 68 that allows humeral cut guide member 54 to be manipulated by the surgeon into correct alignment on the humeral bone 26. In other words, the surgeon may place a finger-tip upon contact surface 68, which allows the surgeon to more easily orient the humeral cut guide member 54 in a manner that bone-engagement surface 60 properly aligns with bone surface 62 of humeral bone 26.

A curved connecting member 70 extends away from bone-engagement member 58 and connects bone-engagement member 58 with a patient-specific pin guide aperture 72. Pin guide aperture 72 is aligned per the specific patient and allows for passage of a drill, Steinmann pin, or guidewire (not shown), that allows humeral bone 26 to be reamed at the appropriate location for any desired resurfacing of humeral bone 26. As illustrated, connecting member 70 is spaced apart from humeral bone 26. It should be understood, however, that connecting member 70 may be designed to abut humeral bone 26. In such a case, connecting member 70 may also include a patient-specific mating surface that is designed to mate and nest with humeral bone 26 in a single position.

A registration member 74 extends away from bone-engagement member 58 in a direction different from that of connecting member 70. Similar to bone-engagement member 58, registration member 74 includes a bone-engagement surface 76 that is designed to mate and nest with humeral bone 26 in a single position. Specifically, bone-engagement surface 76 of registration member 74 is patient-specifically sized and shaped to mate with the bicipital groove 78 (see, e.g., FIG. 6) of humeral bone 26. Thus, registration member 74 is an elongated tab-shaped member having a proximal end 80 unitary or connected to bone-engagement member 58 and a distal end 82 located away from bone-engagement member 58. With the pie-shaped bone-engagement member 58 and elongated registration member 74, humeral cut guide member 54 is configured to nest with humeral head 26 in a single position with as little material as possible. In this manner, a majority (i.e., at least 75%) of humeral head 26 is exposed during the surgical procedure to allow the surgeon greater visual access to the humeral head 26.

Humeral cut guide member 54 includes a cut guide plate 84 including an elongated slot 86. As best shown in FIG. 5, cut guide plate 84 is unitary or connected to bone-engagement member 58 with a cylindrically-shaped member 88 that extends outward from bone-engagement member 58 in a direction different from each of connecting member 70 and registration member 74. Cylindrically-shaped member 88 extends outward from bone-engagement member 88 to an extent that cut guide plate 84 will be spaced apart from humeral head 26. By spacing cut guide plate 84 away from humeral head 26, the unnecessary removal of soft-tissue (e.g., muscle, cartilage, etc.) from humeral head 26 is prevented, which assists in the patient's recovery after the arthroplasty. It should be understood, however, that cut guide plate 84 may be configured to abut humeral bone 26 during pre-operative design of humeral cut guide system 52, if desired.

Cut guide plate 84 includes an upper surface 90 and a lower surface 92, with elongated slot 86 positioned therebetween. Upper surface 90 includes a reinforcing rib 94 extending along an entire length of upper surface 90. Lower surface 92 defines a pair of tube-shaped apertures 96. Tube-shaped apertures are configured to receive a drill (not shown) for drilling humeral bone 26. After drilling of the humeral bone 26, a pair of pins (not shown) such as Steinmann pins or K-wires may be implanted in humeral bone 26, which may be used to assist in securing humeral cut guide member 54 to humeral bone 26. Alternatively, the pair of pins may be used to support a secondary cut guide (not shown) that is configured to assist in resecting or resurfacing of the humeral bone 26 at a different angle in comparison to the angle defined by humeral cut guide member 54. An exemplary secondary cut guide may be found in U.S. Ser. No. 14/265,577 assigned to Biomet Manufacturing, LLC. In this regard, after implantation of the pins, the humeral cut guide member 54 may be removed from humeral bone 26 with the pins remaining in place. The secondary cut guide may then be mated with the pins relative to the humeral bone 26.

Although not required, lower surface 92 may extend outward relative to upper surface 90 such that a shelf or platform 98 is formed. Platform 98 allows for a greater amount of surface area for the tool blade (not shown) to lie upon during resurfacing or resecting of the humeral bone 26. In this manner, the tool blade is substantially prevented from being improperly angled during the resurfacing or resecting of the humeral bone 26 to form planar surface 50. It should be understood that if platform 98 is used, upper surface 90 and reinforcing rib 94 may be omitted. In such a configuration, the tool blade would simply lie upon platform 98 during resurfacing or resecting of the humeral bone 26.

Figure 6:
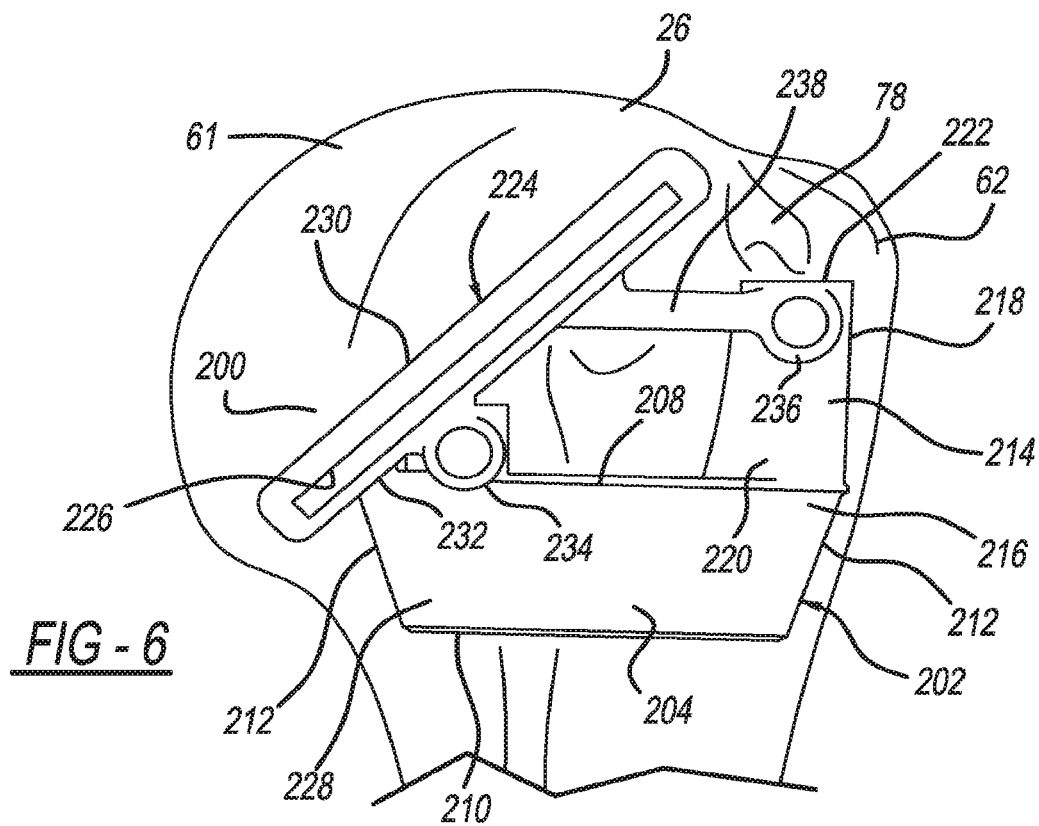
FIG. 6 is a perspective environmental view of a humeral cut guide member according to a second embodiment of the present disclosure.
Figure 7:
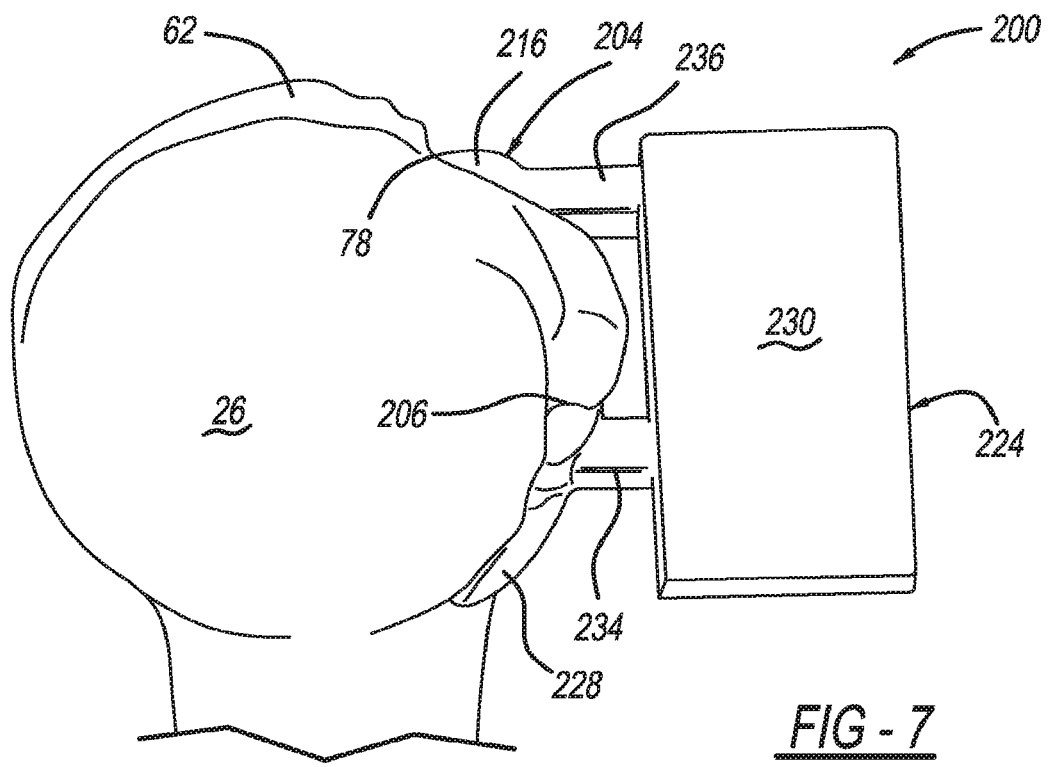
FIG. 7 is another perspective environmental view of the humeral cut guide member according to the second embodiment of the present disclosure.
Figure 8:
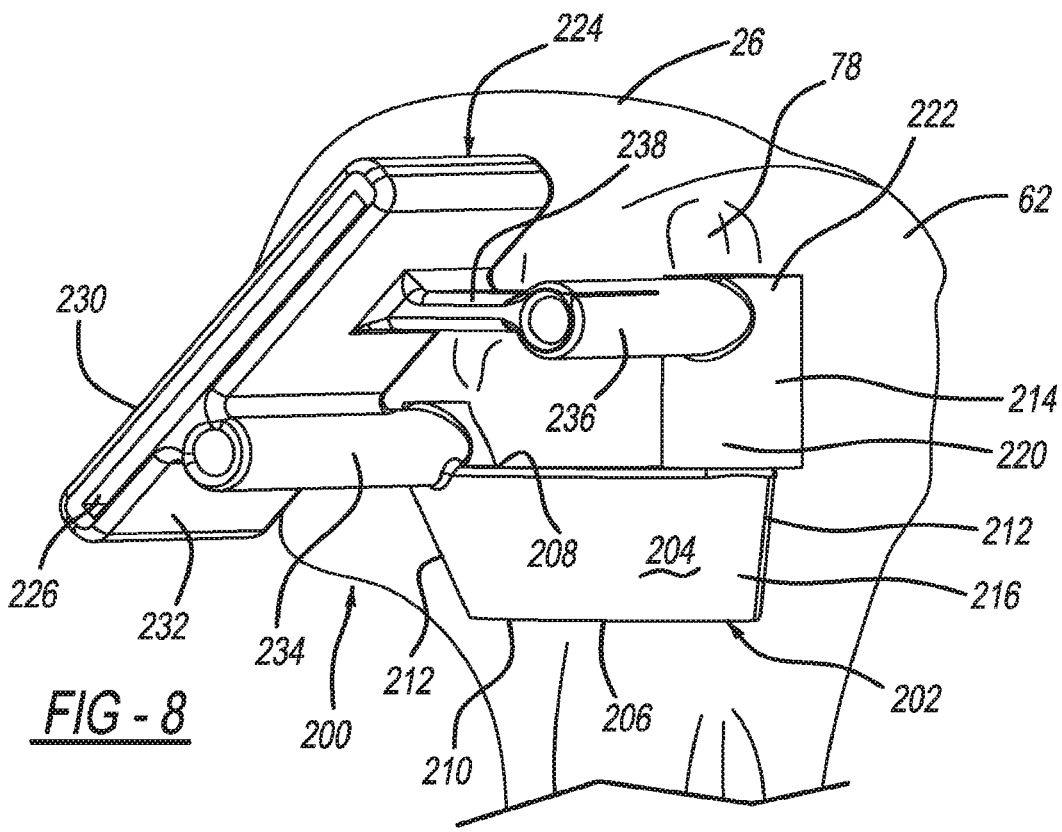
FIG. 8 is another perspective environmental view of the humeral cut guide member according to the second embodiment of the present disclosure.

Now referring to FIGS. 6-8, another exemplary humeral cut guide system 200 is illustrated. Humeral cut guide system 200 includes a humeral cut guide member 202. Humeral cut guide member 202 is configured to be patient-specific such that humeral cut guide member 202 mates with and nests in only one position on humeral bone 26. In this regard, humeral cut guide member 202 includes a bone-engagement member 204 having a bone-engagement surface 206 that is complementary and made to substantially mate and nest in only one position (i.e., as a substantially negative or mirror or inverse surface) with a three-dimensional bone surface 61 of humeral bone 26 with or without associated soft tissues, which is reconstructed as a 3-D image via the aforementioned CAD or software.

As best illustrated in FIG. 6, bone-engagement member 204 and bone-engagement surface 206 are specifically designed to mate and nest on a distal portion of the lesser tuberosity 62 of humeral bone 26. In this regard, a bone-engagement member 204 is a curved member including an upper edge 208 located adjacent the distal portion of the less tuberosity 62, an opposing lower edge 210, and side edges 212.

As best illustrated in, for example, FIGS. 7 and 8, bone-engagement member 204 wraps about a portion of humeral bone 26 in the medial direction from the bicipital groove 78. A registration member 214 is located at a first end 216 of bone-engagement member 204. Registration member 214 extends away from upper edge 208 of bone-engagement member 204 in a direction substantially orthogonal to bone-engagement member 204. Similar to bone-engagement member 204, registration member 214 includes a bone-engagement surface 218 that is designed to mate and nest with humeral bone 26 in a single position.

Specifically, bone-engagement surface 218 of registration member 214 is patient-specifically sized and shaped to mate with the bicipital groove 78 of humeral bone 26. Thus, registration member 214 is an elongated tab-shaped member having a proximal end 220 unitary or connected to bone-engagement member 214 and a distal end 222 located away from upper edge 208. With the bone-engagement member 204 and elongated registration member 214, humeral cut guide member 204 is configured to nest with humeral head 26 at a position that allows for nearly an entirety (i.e., at least 90%) of humeral head 26 to be exposed during the surgical procedure to allow the surgeon greater visual access to the humeral head 26.

Humeral cut guide member 202 includes a cut guide plate 224 including an elongated slot 226. As best shown in FIG. 8, cut guide plate 224 is unitary or connected to bone-engagement member 214 at a second end 228 of bone-engagement member 214. Specifically, cut guide plate 224 includes an upper surface 230 and a lower surface 232, with elongated slot 226 positioned therebetween. Lower surface 232 defines a first tube-shaped aperture 234 that, in addition to being configured to receive a drill (not shown) for drilling humeral bone 26, connects cut guide plate 224 to second end 228. A second tube-shaped aperture 236 is located at distal end 222 of registration member 214, and is connected to cut guide plate 224 via a connecting arm 238.

Similar to the above-described embodiment illustrated in FIGS. 3-5, after drilling of the humeral bone 26, a pair of pins (not shown) such as Steinmann pins or K-wires may be implanted in humeral bone 26 using first and second tube-shaped apertures 234 and 236, which may be used to assist in securing humeral cut guide member 202 to humeral bone 26. Alternatively and as also described in the exemplary embodiment illustrated in FIGS. 3-5, the pair of pins may be used to support a secondary cut guide (not shown) that is configured to assist in resecting or resurfacing of the humeral bone 26 at a different angle in comparison to the angle defined by humeral cut guide member 202.

Although cut guide plate 224 is illustrated as being spaced apart from humeral head 26, it should be understood that cut guide plate 224 may be configured to abut humeral bone 26 during pre-operative design of humeral cut guide system 52, if desired. By spacing cut guide plate 224 away from humeral head 26, however, the unnecessary removal of soft-tissue (e.g., muscle, cartilage, etc.) from humeral head 26 is prevented, which assists in the patient's recovery after the arthroplasty. Further, although not required, lower surface 232 may extend outward relative to upper surface 230 such that a shelf or platform 98 (see FIG. 5, described above) is formed. Platform 98 allows for a greater amount of surface area for the tool blade (not shown) to lie upon during resurfacing or resecting of the humeral bone 26. In this manner, the tool blade is substantially prevented from being improperly angled during the resurfacing or resecting of the humeral bone 26 to form planar surface 50.

Still further, it should be understood that humeral cut guide system 200 may include the curved connecting member 70, which may extend away from upper surface 230 of cut guide plate 224 and connect cut guide plate 224 member with a patient-specific pin guide aperture 72 (see, e.g., FIG. 3). The pin guide aperture 72 may be aligned per the specific patient and allows for passage of a drill, Steinmann pin, or guidewire (not shown), that allows humeral bone 26 to be reamed at the appropriate location for any desired resurfacing of humeral bone 26.

Figure 9:
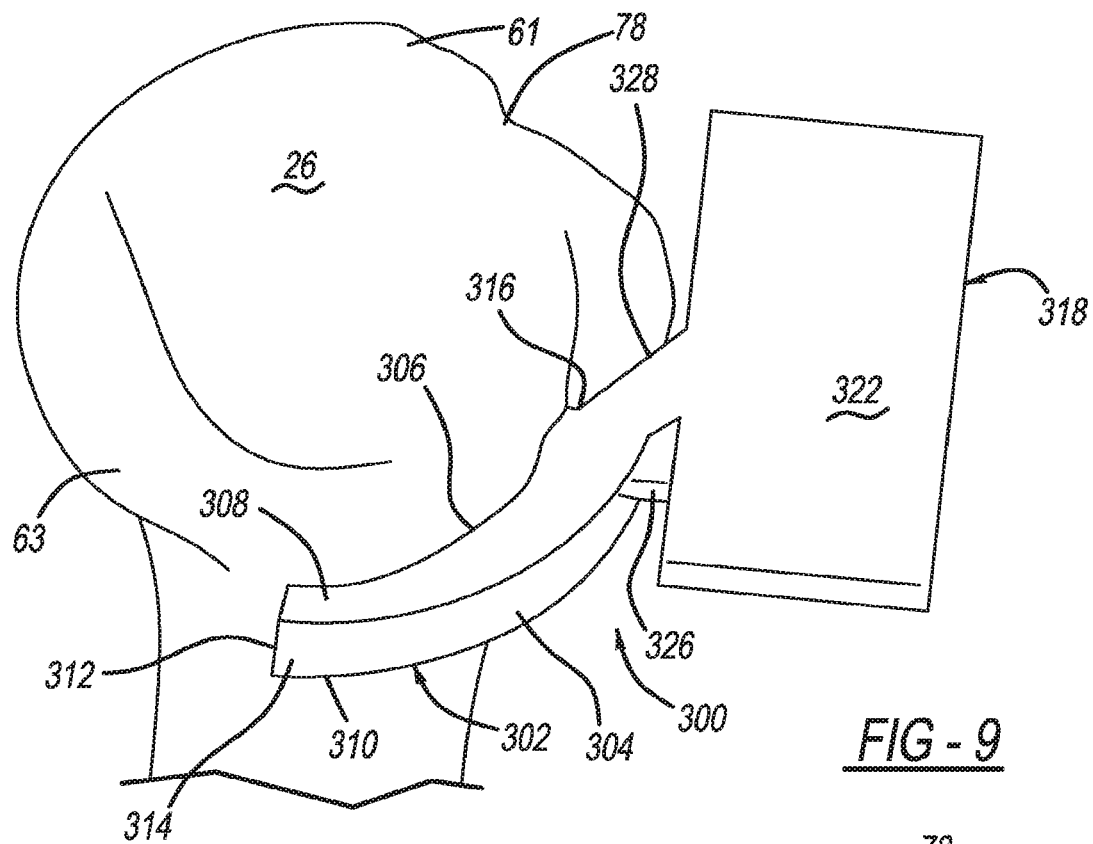
FIG. 9 is a perspective environmental view of a humeral cut guide member according to a third embodiment of the present disclosure.
Figure 10:
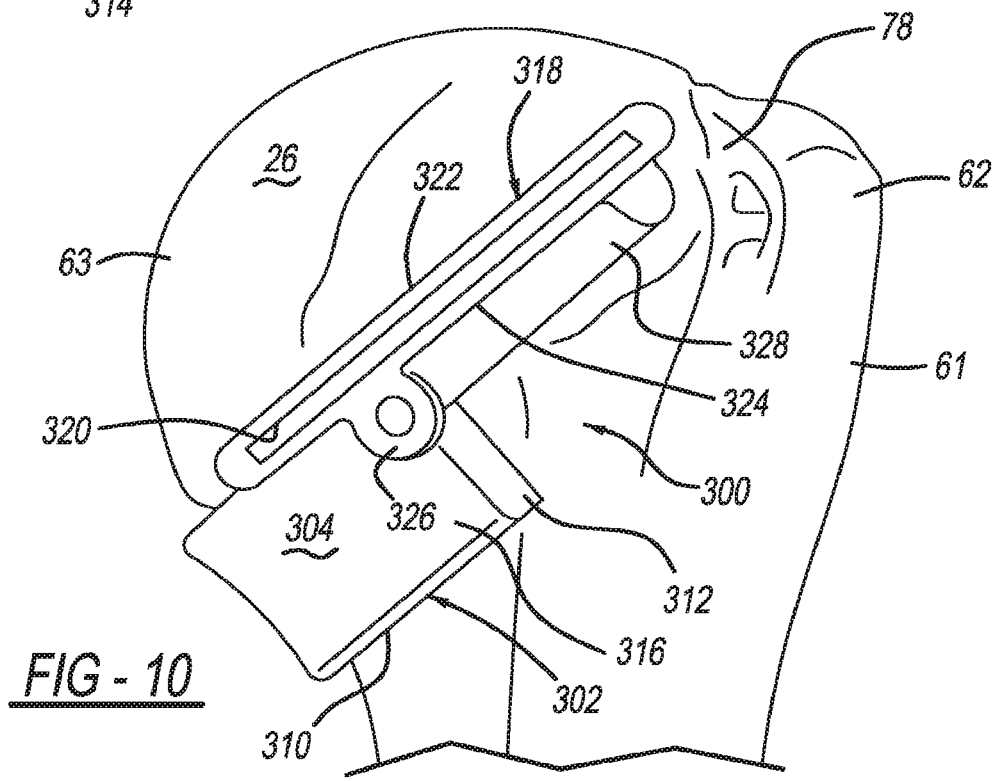
FIG. 10 is another perspective environmental view of the humeral cut guide member according to the third embodiment of the present disclosure.

Now referring to FIGS. 9 and 10, another exemplary humeral cut guide system 300 is illustrated. Humeral cut guide system 300 includes a humeral cut guide member 302. Humeral cut guide member 302 is configured to be patient-specific such that humeral cut guide member 302 mates with and nests in only one position on humeral bone 26. In this regard, humeral cut guide member 302 includes a bone-engagement member 304 having a bone-engagement surface 306 that is complementary and made to substantially mate and nest in only one position (i.e., as a substantially negative or mirror or inverse surface) with a three-dimensional bone surface 62 of humeral bone 26 with or without associated soft tissues, which is reconstructed as a 3-D image via the aforementioned CAD or software.

As best illustrated in FIG. 9, bone-engagement member 304 and bone-engagement surface 306 are specifically designed to mate and nest medially off of the proximal humeral bone 26. In this regard, a bone-engagement member 304 is a curved member including an upper edge 308 located adjacent the distal portion of the greater tuberosity 63, an opposing lower edge 310, and side edges 312. Bone-engagement member 304 wraps about a portion of humeral bone 26 laterally from the distal portion of the greater tuberosity 63 in a direction toward bicipital groove 78, and includes a first end 314 and a second end 316. Extending from second end 316 is a cut guide plate 318 including an elongated slot 320.

As best shown in FIG. 9, cut guide plate 318 is unitary or connected to bone-engagement member 304 at a second end 316. Cut guide plate 318 includes an upper surface 322 and a lower surface 324, with elongated slot 320 positioned therebetween. Lower surface 322 defines a first tube-shaped aperture 326 that is configured to receive a drill (not shown) for drilling humeral bone 26, and after drilling of the humeral bone 26, is configured to receive a pin (not shown) that is operable to secure humeral cut guide member 302 to the humeral bone 26. A second tube-shaped aperture 328 may also be formed at second end 316 that is configured to receive a drill (not shown) for drilling humeral bone 26, and after drilling of the humeral bone 26, is configured to receive a pin (not shown) that is operable to secure humeral cut guide member 302 to the humeral bone 26. The above-noted configuration allows for nearly an entirety (i.e., at least 90%) of humeral head 26 to be exposed during the surgical procedure to allow the surgeon greater visual access to the humeral head 26.

Although not illustrated, it should be understood that humeral cut guide system 300 may include the curved connecting member 70, which may extend away from upper surface 322 of cut guide plate 318 and connect cut guide plate 318 with a patient-specific pin guide aperture 72 (see, e.g., FIG. 3). The pin guide aperture 72 may be aligned per the specific patient and allows for passage of a drill, Steinmann pin, or guidewire (not shown), that allows humeral bone 26 to be reamed at the appropriate location for any desired resurfacing of humeral bone 26. Alternatively, the curved connecting member 70 and pin guide aperture 72 may extend from upper edge 308 at a location positioned proximate first end 314.

In addition, although cut guide plate 318 is illustrated as being spaced apart from humeral head 26, it should be understood that cut guide plate 318 may be configured to abut humeral bone 26 during pre-operative design of humeral cut guide system 300, if desired. By spacing cut guide plate 318 away from humeral head 26, the unnecessary removal of soft-tissue (e.g., muscle, cartilage, etc.) from humeral head 26 is prevented, which assists in the patient's recovery after the arthroplasty. Further, although not required, lower surface 322 may extend outward relative to upper surface 320 such that a shelf or platform 98 (see FIG. 5, described above) is formed. Platform 98 allows for a greater amount of surface area for the tool blade (not shown) to lie upon during resurfacing or resecting of the humeral bone 26. In this manner, the tool blade is substantially prevented from being improperly angled during the resurfacing or resecting of the humeral bone 26 to form planar surface 50.

Figure 11:
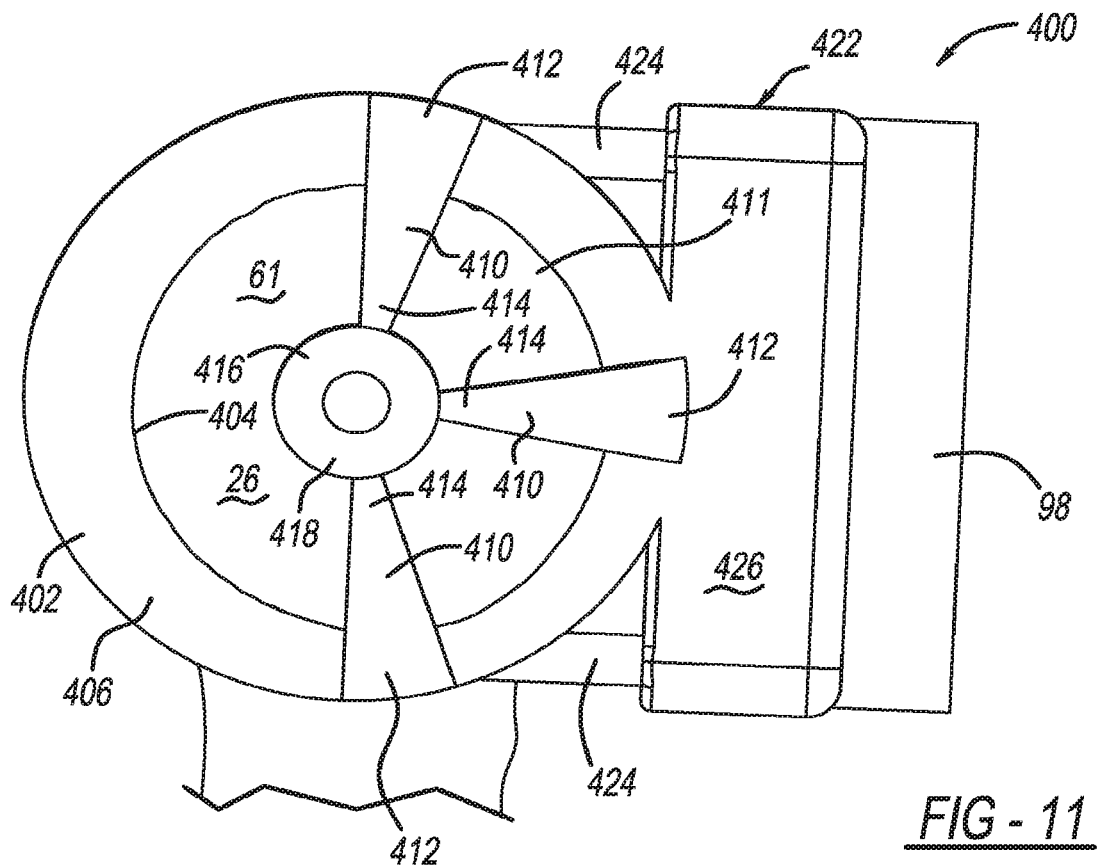
FIG. 11 is a perspective environmental view of a humeral cut guide member according to a fourth embodiment of the present disclosure.
Figure 12:
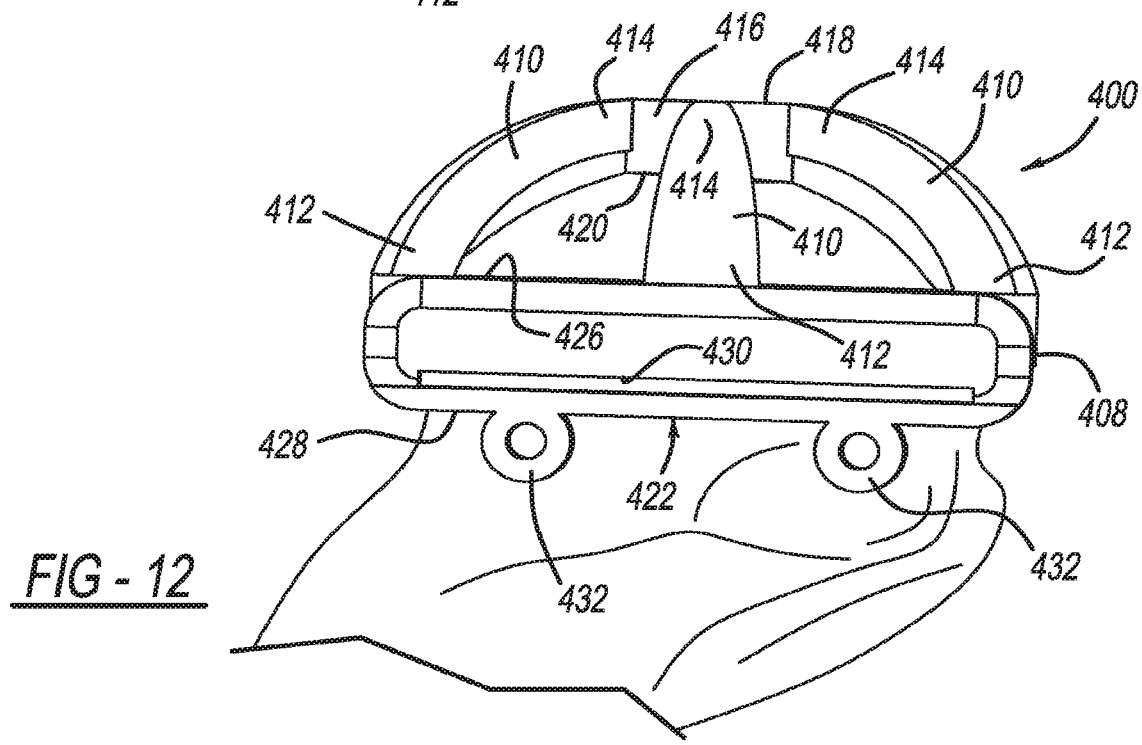
FIG. 12 is another perspective environmental view of the humeral cut guide member according to the fourth embodiment of the present disclosure.
Figure 13:
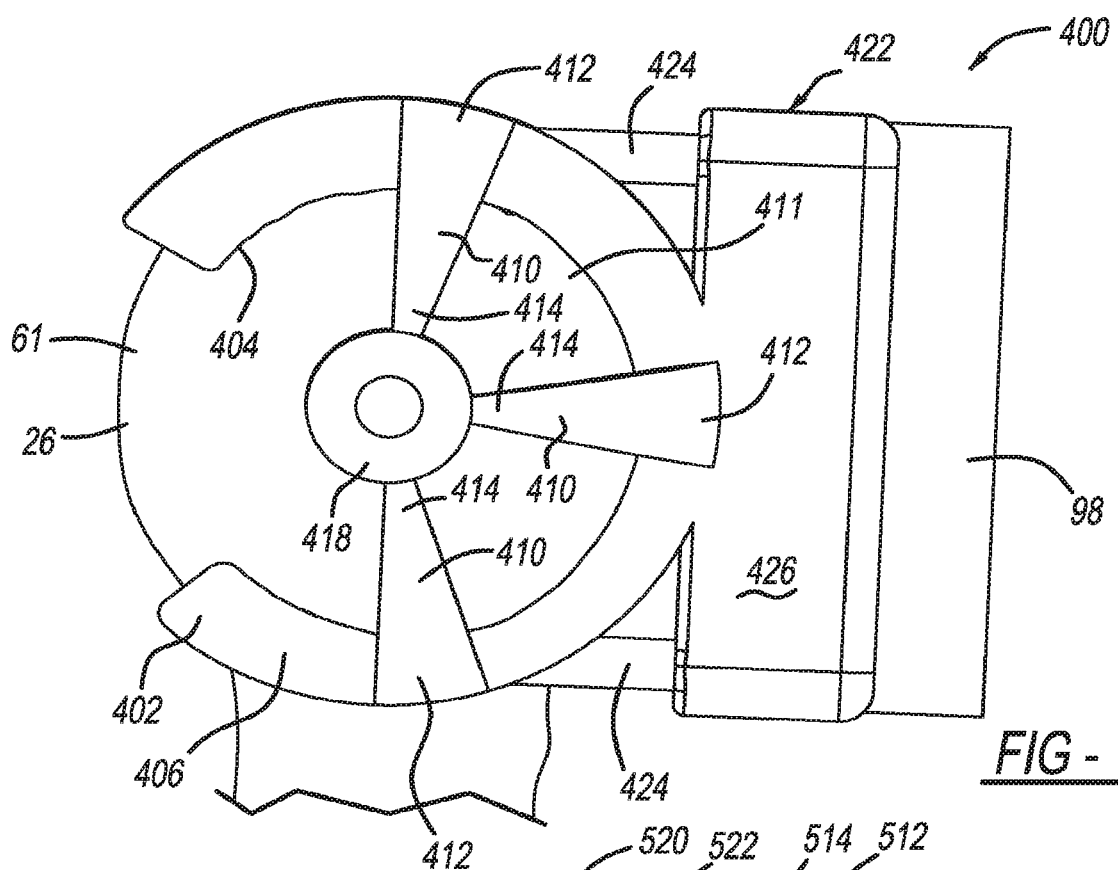
FIG. 13 is another perspective environmental view of a modified humeral cut guide member according to the fourth embodiment of the present disclosure.

Now referring to FIGS. 11 and 12, another exemplary humeral cut guide system 400 according to an aspect of the present disclosure is illustrated. Humeral cut guide system 400 includes a ring-shaped patient-specific humeral cut guide member 402 that encircles the greater tuberosity 63 of the humeral head 26. Humeral cut guide member 402 is patient-specific and includes a bone-engagement surface 404 that is complementary and made to substantially mate and nest in only one position (i.e., as a substantially negative or mirror or inverse surface) with a three-dimensional bone surface 61 of humeral bone 26 with or without associated soft tissues, which is reconstructed as a 3-D image via the aforementioned CAD or software. Although humeral cut guide member 402 is illustrated as being ring-shaped, it should be understood that humeral cut guide member 402 may be horseshoe-shaped (FIG. 13), if desired.

Humeral cut guide member 402, in addition to bone-engagement surface 404, includes an upper surface 406 and a lower surface 408. Extending radially inward and over humeral head 26 toward a center of humeral cut guide member 402 are a plurality of pie-shaped ribs 410. Ribs 410 may include a wider proximal portion 412 unitary with humeral cut guide member 402 and a narrower distal portion 414. Alternatively, ribs 410 may include the same width along the entire length thereof. Although only three ribs 410 are illustrated in FIGS. 11 and 12, it should be understood that a greater or lesser number of ribs 410 may be used, without departing from the scope of the present disclosure. Regardless, spaces 411 between ribs 410 allow for easier viewing of humeral head 26 by the surgeon during the surgical procedure. In this regard, humeral cut guide member 402 is designed such that at least 50% of the humeral head 26 is exposed or visible when humeral cut guide member 402 is mated thereto.

The distal portions 414 terminate at a patient specific pin guide aperture 416. Pin guide aperture 416 may be aligned per the specific patient and allows for passage of a drill, Steinmann pin, or guidewire (not shown), that allows humeral bone 26 to be reamed at the appropriate location for any desired resurfacing of humeral bone 26. Pin guide aperture 416 includes an exterior surface 418 and a bone-engagement surface 420. Bone-engagement surface 420 may be patient specifically designed pre-operatively. Further, although ribs 410 are illustrated as being spaced apart from humeral head 26, it should be understood that ribs 410 may abut humeral head 26 with a patient specific bone-engagement surface as well.

A cut guide plate 422 is unitary or connected to humeral cut guide member 402 by a pair of connection members 424 such that cut guide plate 422 is spaced apart from humeral bone 26. By spacing cut guide plate 422 away from humeral head 26, the unnecessary removal of soft-tissue (e.g., muscle, cartilage, etc.) from humeral head 26 is prevented, which assists in the patient's recovery after the arthroplasty. Cut guide plate 422 includes an upper surface 426 and a lower surface 428, with an elongated slot 430 positioned therebetween. Lower surface 428 defines a pair of tube-shaped apertures 432 that are configured to receive a drill (not shown) for drilling humeral bone 26. After drilling of the humeral bone 26, the tube-shaped apertures 432 are configured to receive a pin (not shown) that is operable to secure humeral cut guide member 402 to the humeral bone 26. The above-noted configuration allows for a majority of humeral head 26 to be exposed during the surgical procedure to allow the surgeon greater visual access to the humeral head 26.

Although cut guide plate 422 is illustrated as being spaced apart from humeral head 26, which is desirable to preserve soft tissue as noted above, it should be understood that cut guide plate 422 may be configured abut humeral bone 26 during pre-operative design of humeral cut guide system 400, if desired. Further, although not required, lower surface 428 may extend outward relative to upper surface 426 such that a shelf or platform 98 is formed. Platform 98 allows for a greater amount of surface area for the tool blade (not shown) to lie upon during resurfacing or resecting of the humeral bone 26. In this manner, the tool blade is substantially prevented from being improperly angled during the resurfacing or resecting of the humeral bone 26 to form planar surface 50.

Moreover, although not illustrated in FIGS. 11 and 12, it should be understood that humeral cut guide member 402 may include a registration member (see, e.g., the registration member 74 in FIG. 3) similar to those described above. That is, humeral cut guide member 402 may include registration member (not shown) that extends away from humeral cut guide member 402 in a direction different from that ribs 410 including a bone-engagement surface 76 that is designed to mate and nest with the bicipital groove 78 of humeral bone 26.

Now referring to FIGS. 14-20, another exemplary humeral cut guide system 500 according to an aspect of the present disclosure is illustrated. Humeral cut guide system 500 includes a patient-specific humeral cut guide member 502. Humeral cut guide member 502 is configured to be patient-specific such that humeral cut guide member 502 mates with and nests in only one position on humeral bone 26. In this regard, humeral cut guide member 502 includes a bone-engagement member 504 having a bone-engagement surface 506 that is complementary and made to substantially mate and nest in only one position (i.e., as a substantially negative or mirror or inverse surface) with a three-dimensional bone surface 62 of humeral bone 26 with or without associated soft tissues, which is reconstructed as a 3-D image via the aforementioned CAD or software.

Figure 14:
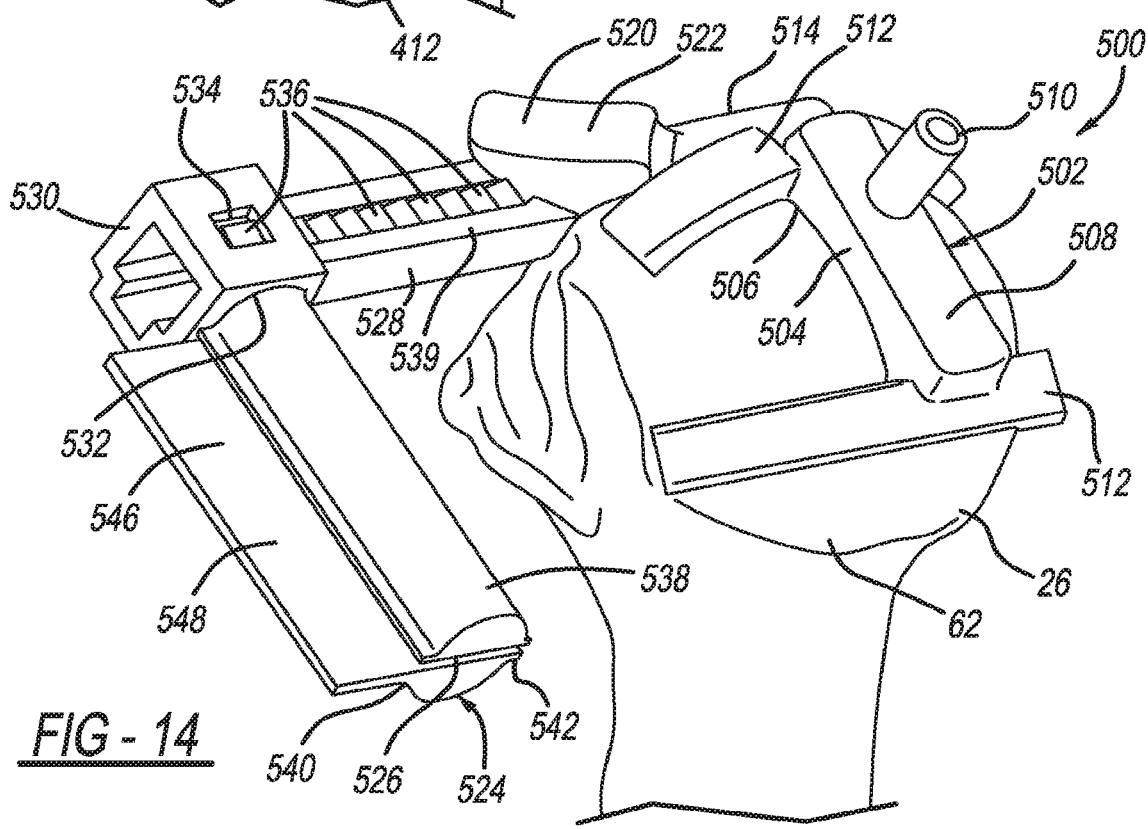
FIG. 14 is a perspective environmental view of a humeral cut guide member according to a fifth embodiment of the present disclosure.
Figure 15:
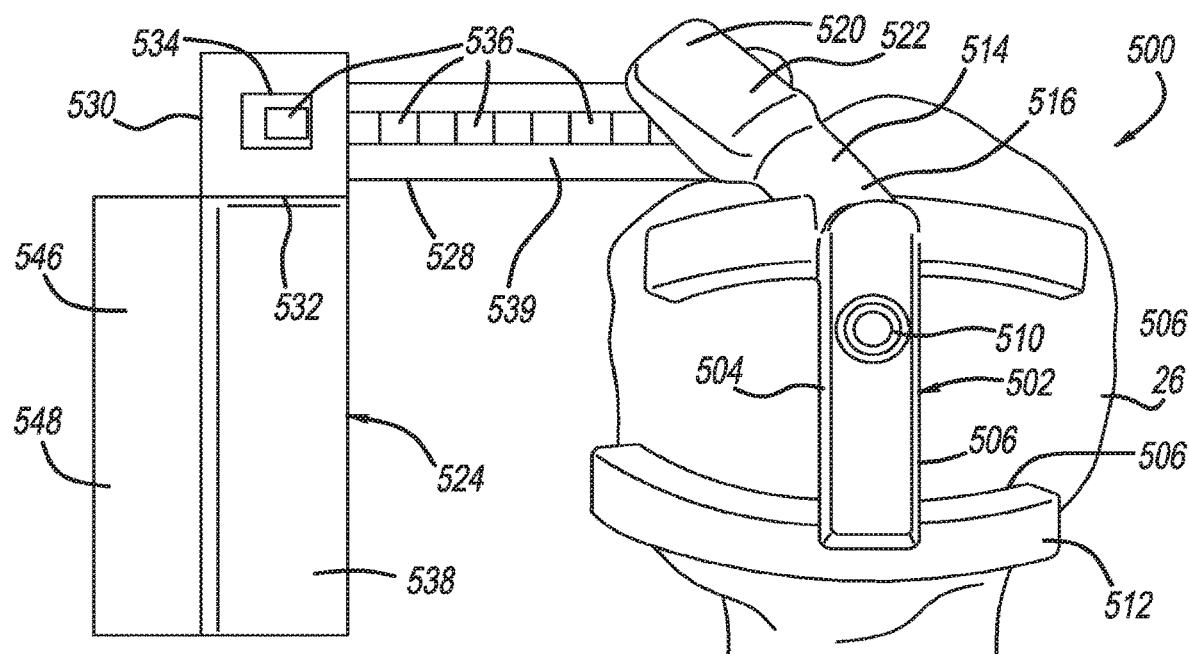
FIG. 15 is another perspective environmental view of the humeral cut guide member according to the fifth embodiment of the present disclosure.

As best illustrated in FIG. 14, bone-engagement member 504 includes an elongated primary member 508 extending in a first direction (i.e., a direction parallel with a coronal plane of the body) over humeral head 26, including a pin guide aperture 510. Pin guide aperture 510 is aligned per the specific patient and allows for passage of a drill, Steinmann pin, or guide wire (not shown), that allows humeral bone 26 to be reamed at the appropriate location for any desired resurfacing of humeral bone 26. Bone-engagement member 504 also includes a pair of secondary members 512 extending substantially orthogonal to primary member 508. Secondary members 512 define a portion of bone-engagement surface 506, and assist in mating and nesting humeral cut guide member 502 in only one position on humeral bone 26 with or without associated soft tissues.

Bone-engagement member 504 also includes a registration member 514 that is patient-specifically sized and shaped to mate with the bicipital groove 78 of humeral bone 26. Thus, registration member 514 is an elongated tab-shaped member having a proximal end 516 unitary or connected to bone-engagement member 504 and a distal end 518 located away from bone-engagement member 504. With the primary member 508, secondary members 512, and elongated registration member 514, humeral cut guide member 504 is configured to nest with humeral head 26 in a single position with as little material as possible. In this manner, a majority of humeral head 26 is exposed during the surgical procedure to allow the surgeon greater visual access to the humeral head 26. In this regard, humeral cut guide member 502 is designed such that at least 60% of the humeral head 26 is exposed or visible when humeral cut guide member 402 is mated thereto.

Registration member 514 may also define a protrusion 520 that provides a curved contact surface 522 that allows humeral cut guide member 504 to be manipulated by the surgeon into correct alignment on the humeral bone 26. In other words, the surgeon may place a finger-tip upon contact surface 522, which allows the surgeon to more easily orient the humeral cut guide member 504 in a manner that bone-engagement surface 506 properly aligns with bone surface 62 of humeral bone 26.

Humeral cut guide member 502 includes a cut guide plate 524 including an elongated slot 526. As best shown in FIGS. 14, 15, 18, and 19, cut guide plate 524 is connected to bone-engagement member 504 with a tube-shaped member 528 that extends outward from registration member 514 such that cut guide plate 524 may be spaced apart from humeral head 26. By spacing cut guide plate 524 away from humeral head 26, the unnecessary removal of soft-tissue (e.g., muscle, cartilage, etc.) from humeral head 26 is prevented, which assists in the patient's recovery after the arthroplasty. Although tube-shaped member 528 extends outward from bone-engagement member 504 to an extent that cut guide plate 524 will be spaced apart from humeral head 26, it should be understood, however, that the location of cut guide plate 524 may be adjusted along tube-shaped member 528 such that cut guide plate 524 may be moved closer to humeral bone 26, if desired.

More specifically, cut guide plate 524 includes a connection portion 530 at an end 532 thereof that is configured to mate with tube-shaped member 528. Further, connection portion 530 may include a mating aperture 534 that is designed to mate with one of a plurality of protrusions 536 formed along a surface 539 of tube-shaped member 528. In this regard, connection portion 530 may be urged along tube-shaped member 528 to adjust the position of cut guide plate 524 relative to humeral head 26. As connection portion 530 is urged along tube-shaped member 528, the mating aperture 534 will mate with protrusions 536 such that connection portion 530 may be positioned at the selected protrusion 536. Connection portion 530 may then only be moved when a force sufficient to disengage the mating aperture 534 from the selected protrusion 536 is provided to the connection portion 530. In this manner, the position of cut guide plate 524 may be selectively adjusted based on the preferences of the surgeon during the shoulder arthroplasty. It should be understood that although cut guide plate 524 has been described above as being movable along tube-shaped member 528, the present disclosure contemplates configurations where cut guide plate 524 is immovably fixed to tube-shaped member 528.

Figure 16:
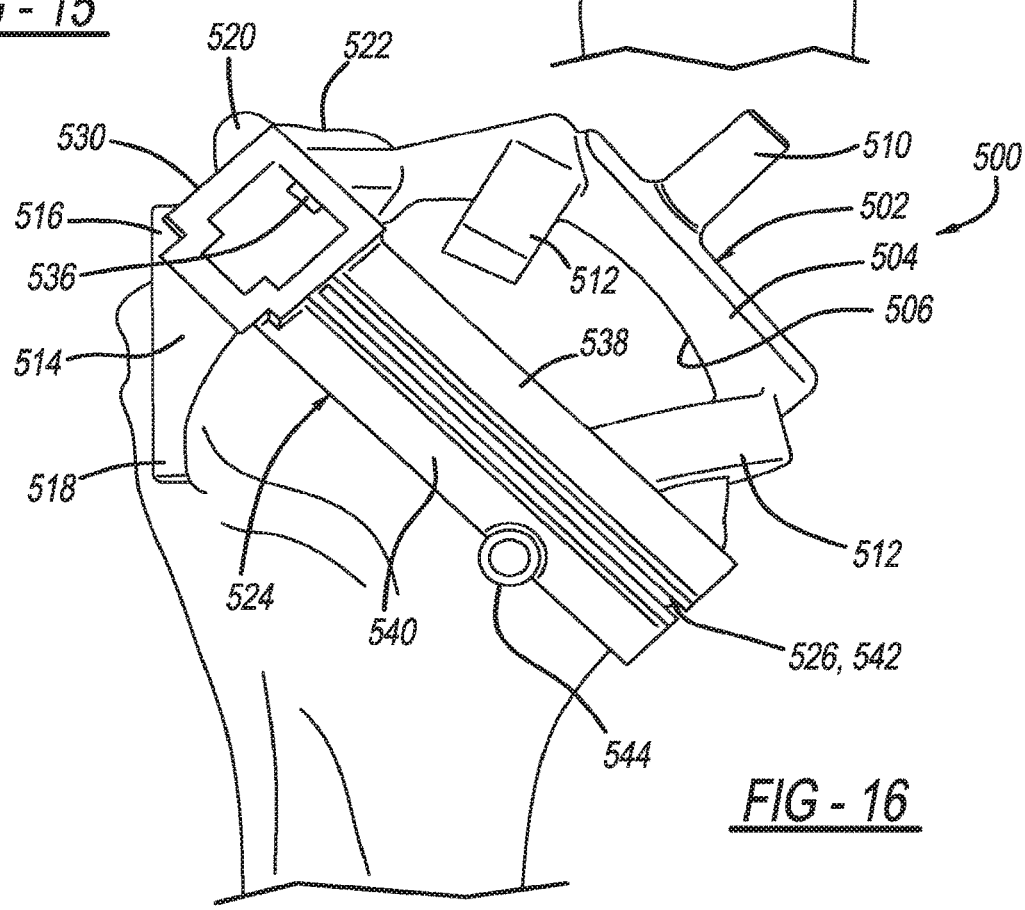
FIG. 16 is another perspective environmental view of the humeral cut guide member according to the fifth embodiment of the present disclosure.
Figure 17:
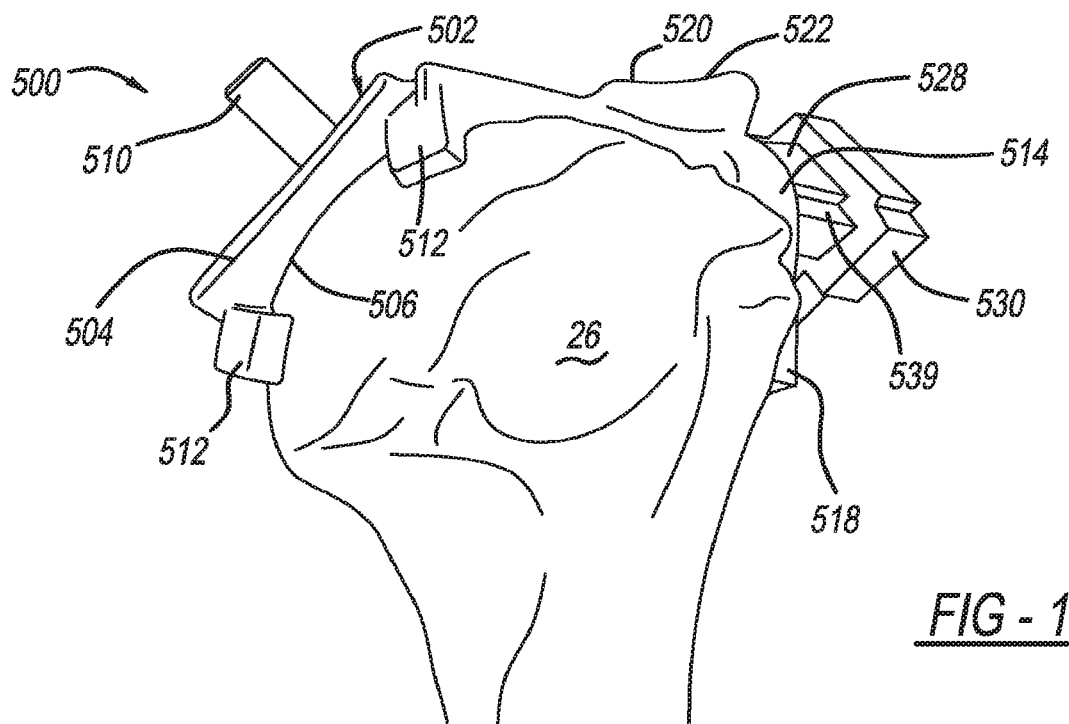
FIG. 17 is another perspective environmental view of the humeral cut guide member according to the fifth embodiment of the present disclosure.
Figure 18:
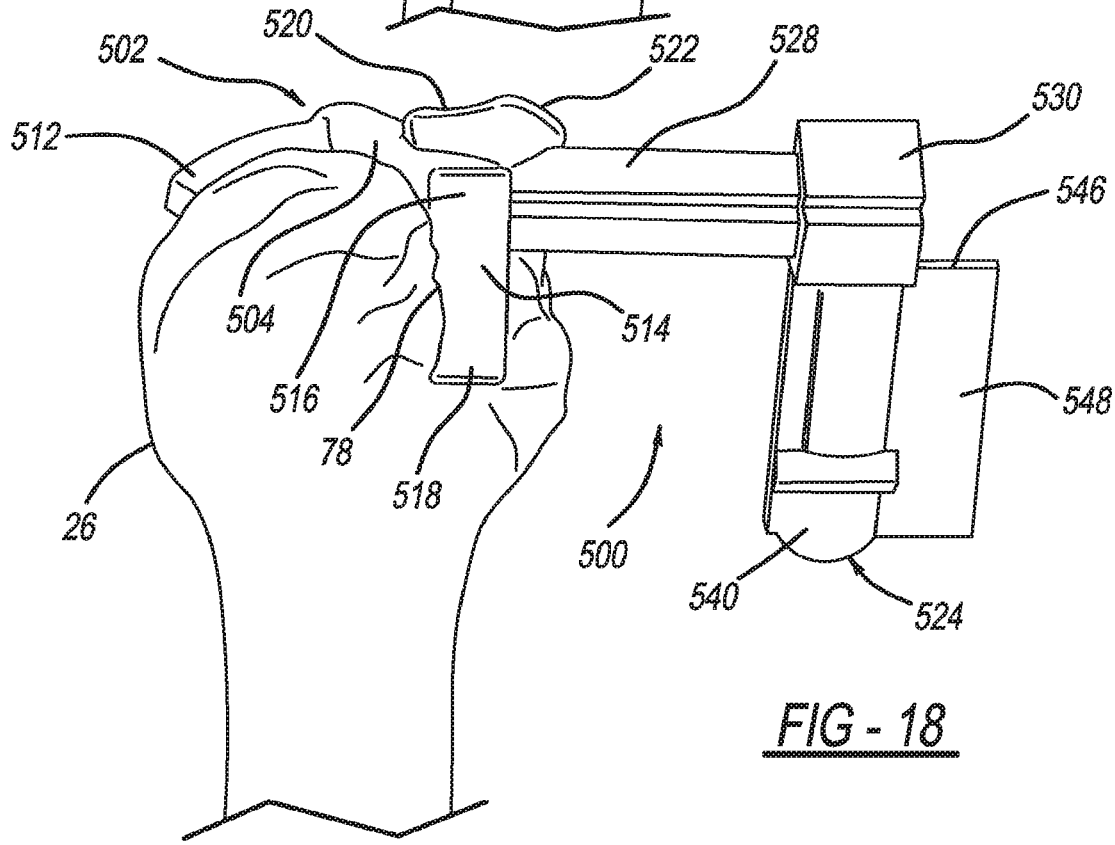
FIG. 18 is another perspective environmental view of the humeral cut guide member according to the fifth embodiment of the present disclosure.
Figure 19:
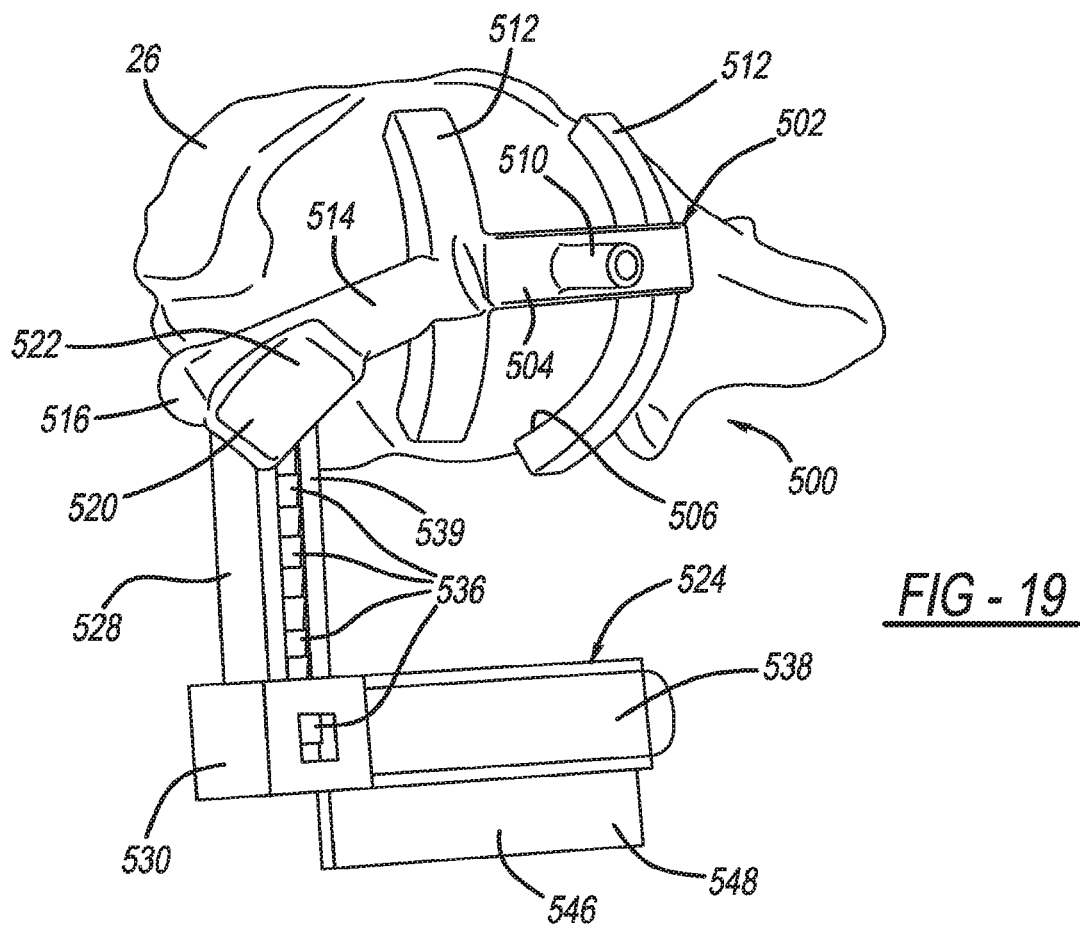
FIG. 19 is another perspective environmental view of the humeral cut guide member according to the fifth embodiment of the present disclosure.

As best shown in FIG. 16, cut guide plate 524 includes an upper member 538 spaced apart from a lower member 540, with elongated slot 526 defined by a gap 542 between upper member 538 and lower member 540. Lower member 540 defines an elongated aperture 544 that is configured to receive a drill (not shown) for drilling humeral bone 26. After drilling of the humeral bone 26, a pin (not shown) such as a Steinmann pin or K-wire may be implanted in humeral bone 26, which may be used to assist in positioning humeral cut guide member 502 relative to humeral bone 26. In the illustrated embodiment, elongated aperture 544 travels parallel to tube-shaped member 528 to allow cut guide plate 524 to move along tube-shaped member 528 without interference from the pin (not shown). If cut guide plate 524 is immovable fixed to tube-shaped member 528, however, it will be appreciated that elongated aperture 544 may extend in a non-parallel manner relative to tube-shaped member 528 to assist in securing cut guide member 502 to humeral bone 526.

Although only a single elongated aperture 544 is illustrated in the figures, it should be understood that a pair of elongated apertures 544 may be used to allow for a pair of pins to be used to support a secondary cut guide (not shown) that is configured to assist in resecting or resurfacing of the humeral bone 26 at a different angle in comparison to the angle defined by humeral cut guide member 502. An exemplary secondary cut guide may be found in U.S. Ser. No. 14/265,577 assigned to Biomet Manufacturing, LLC. In this regard, after implantation of the pins, the humeral cut guide member 502 may be removed from humeral bone 26 with the pins remaining in place. The secondary cut guide may then be mated with the pins relative to the humeral bone 26.

Although not required, lower member 540 may define a surface 546 that extends outward relative to upper member 538 such that a shelf or platform 548 is formed. Platform 548 allows for a greater amount of surface area for the tool blade (not shown) to lie upon during resurfacing or resecting of the humeral bone 26. In this manner, the tool blade is substantially prevented from being improperly angled during the resurfacing or resecting of the humeral bone 26 to form planar surface 50.

Figure 20:
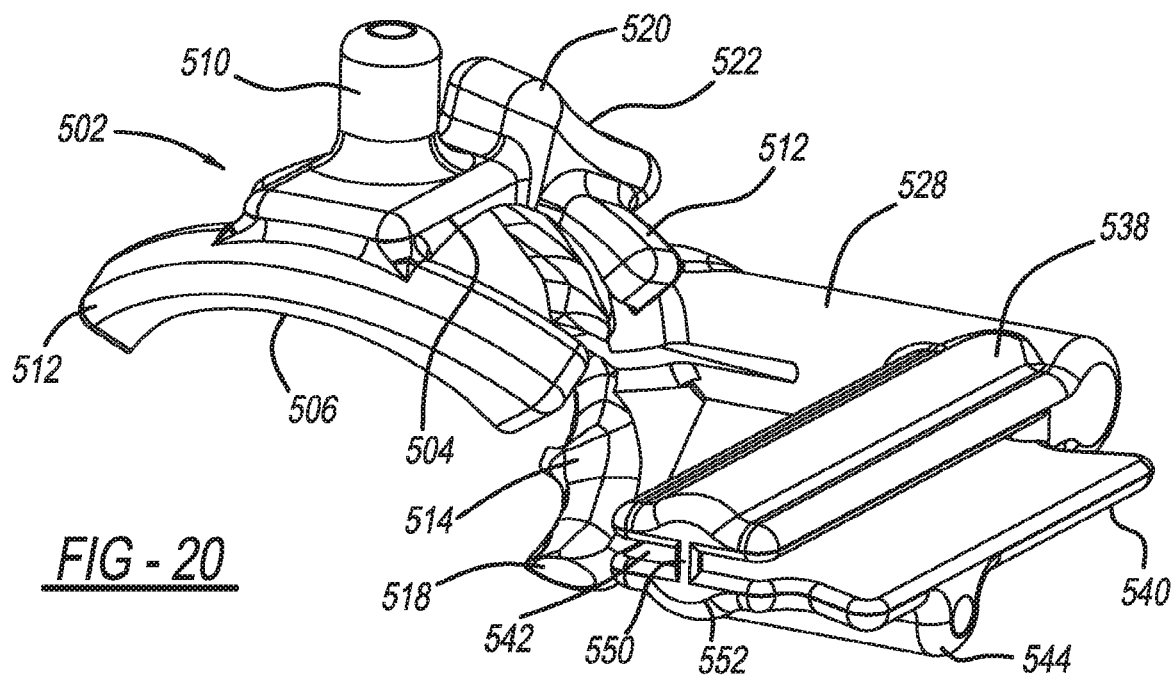
FIG. 20 is a perspective view of a modified humeral cut guide member according to the fifth embodiment of the present disclosure.

Lastly, as best shown in FIG. 20, a support bar 550 may fix upper member 538 to lower member 540. Support bar 550 is formed at an opposite end 552 of cut guide plate 524 relative to tube-shaped member 528, and assist in maintaining the proper gap 542 between upper member 538 and lower member 540. Notwithstanding, it should be understood that support bar 550 is removable during surgery by cutting support bar 550 with the saw or blade for resecting or resurfacing humeral bone 26, as desired by the surgeon. It should be understood that although tube-shaped member 528 is illustrated as fixing cut guide plate 524 in one position relative to humeral head 26, tube-shaped member 528 may be adjustable as illustrated in FIGS. 14-19.

Figure 21A:
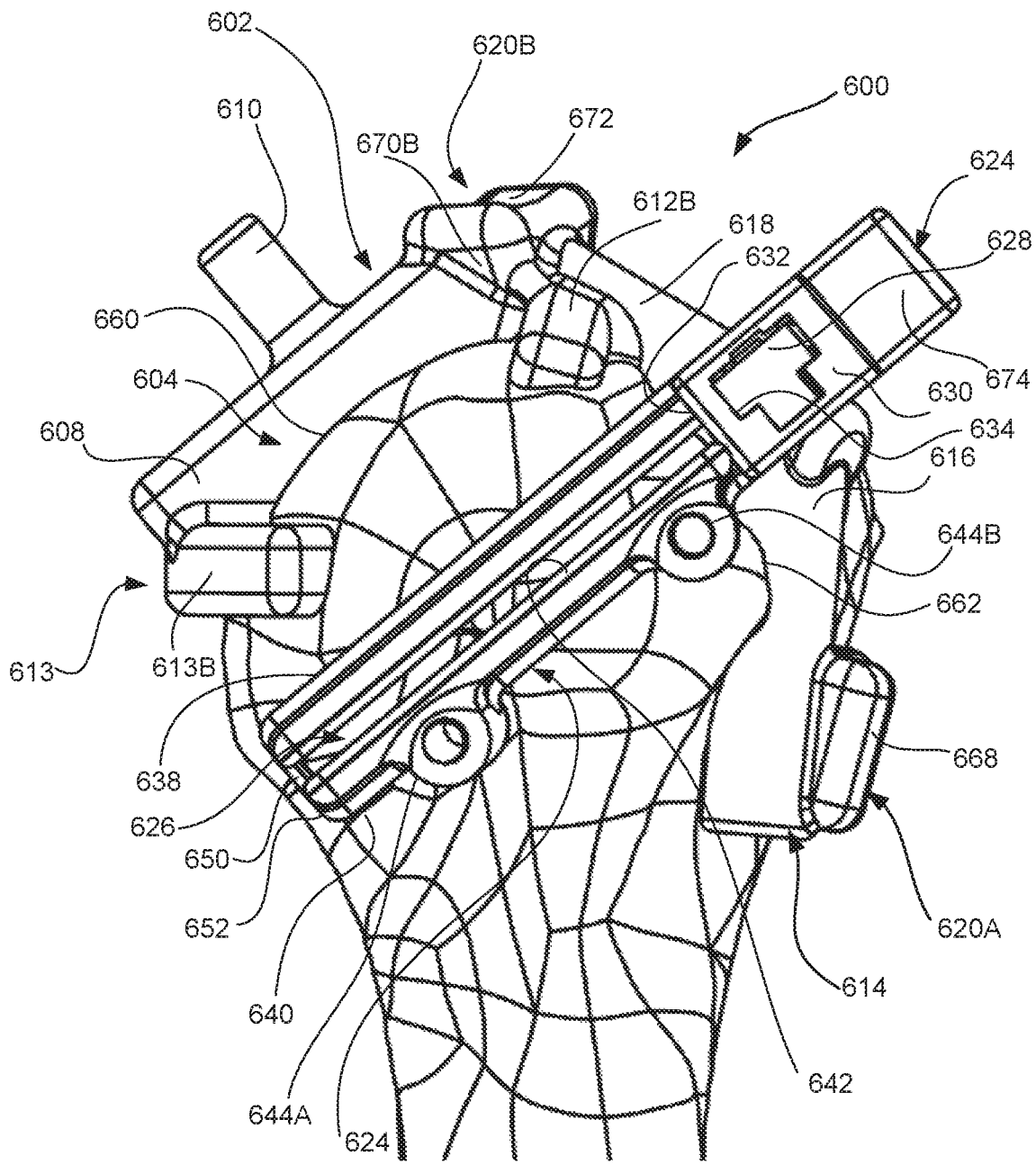
FIG. 21A shows an anterior perspective view of a humeral cut guide system attached to a humeral bone and having a cut guide plate configured to smoothly slide on a cut guide member.
Figure 21B:
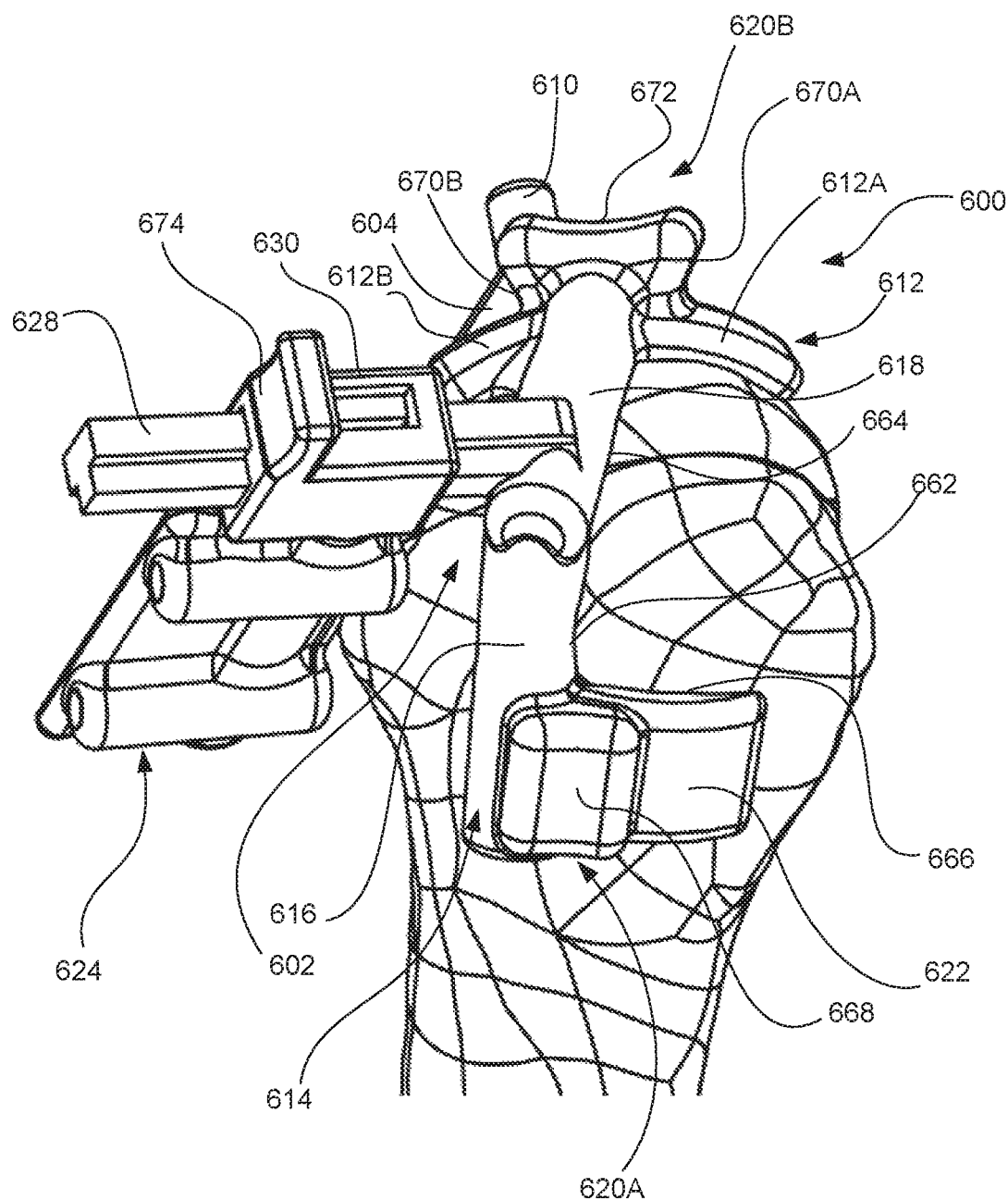
FIG. 21B shows a lateral perspective view of the humeral cut guide system of FIG. 21A having protrusions to facilitate attachment of the system to the humeral bone by a surgeon.
Figure 21C:
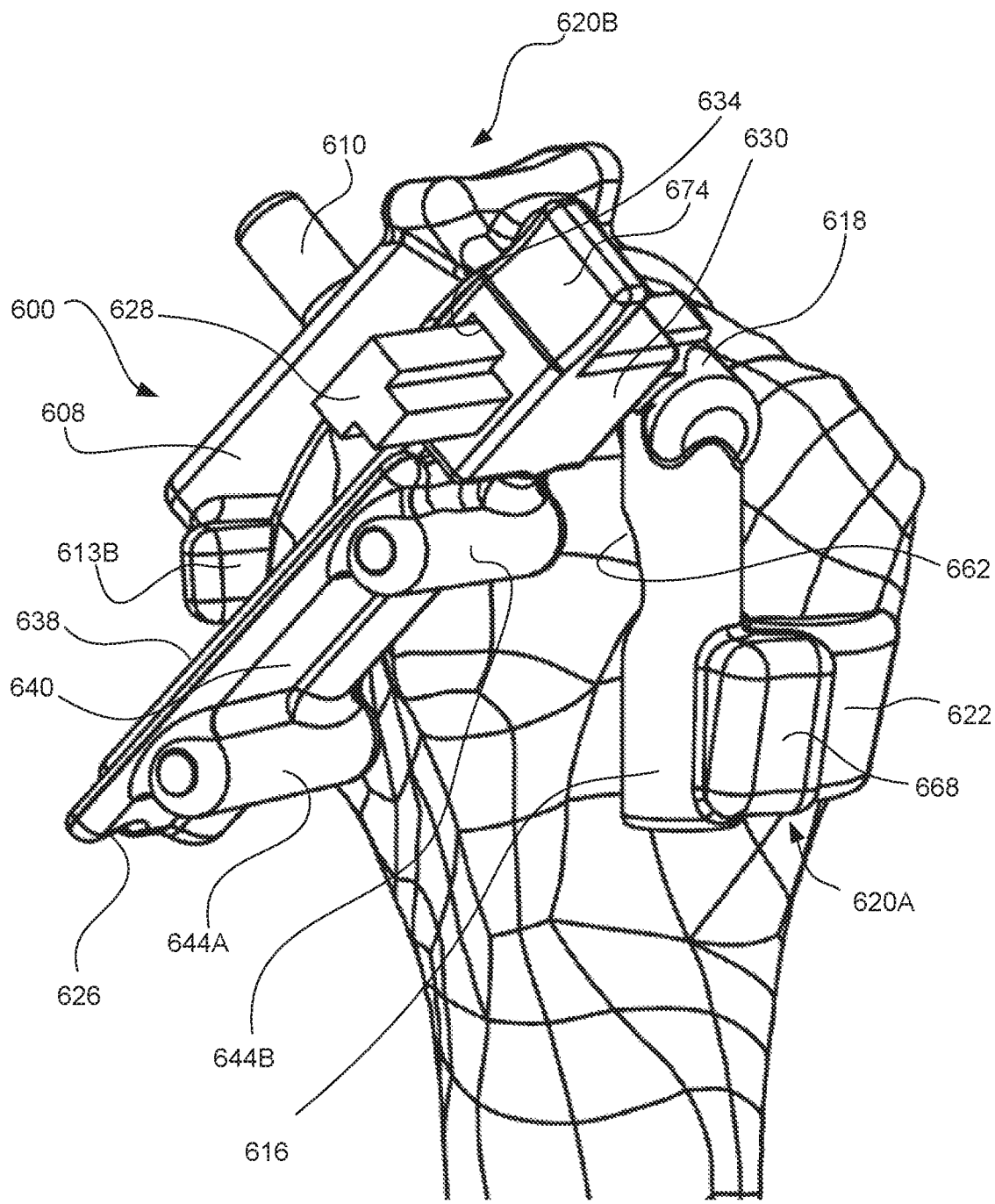
FIG. 21C shows another perspective view of the humeral cut guide system of FIG. 21A attached to the humeral bone to show the cut guide member and the protrusions.

FIG. 21A shows an anterior perspective view of humeral cut guide system 600 attached to humeral bone 26 and having cut guide plate 624 configured to smoothly slide on cut guide member 602. FIG. 21B shows a lateral perspective view of humeral cut guide system 600 attached to humeral bone 26 and having protrusions 620A and 620B to facilitate manipulation of cut guide system 600 by a surgeon. FIG. 21C shows another perspective view of humeral cut guide system 600 attached to humeral bone 26 to show cut guide member 602, cut guide plate 624 and protrusions 620A and 620B.

Humeral cut guide system 600 includes patient-specific humeral cut guide member 602 and cut guide plate 624. Cut guide member 602 includes bone-engagement member 604, which is defined by primary member 608 that includes pin guide 610 and supports 612 and 613. Cut guide member 602 also includes registration member 614, which includes first registration portion 616 and second registration portion 618. Cut guide member 602 also includes first protrusion 620A connected to first registration portion 616, and second protrusion 620B connected between second registration portion 618 and primary member 608. First protrusion 620A includes support 622.

Cut guide plate 624 is connected to cut guide member 602 via elongate member 628. Cut guide plate 624 includes connection portion 630, socket 634, slot 626 defined by gap 642, elongate members 638 and 640, apertures 644A and 644B and support bar 650.

Bone-engagement member 604 includes first patient-specific bone-engagement surface 660. Registration member 614 includes second patient-specific bone-engagement surface 662 and third patient-specific bone-engagement surface 664. Support 622 includes fifth patient-specific bone-engagement surface 666.

Now referring to FIGS. 21A-21C, humeral cut guide system 600 illustrates another example according to an aspect of the present disclosure having smooth elongate member 628 and protrusions 620A and 620B. Humeral cut guide system 600 includes patient-specific humeral cut guide member 602. Humeral cut guide member 602 is configured to be patient-specific such that humeral cut guide member 602 mates with and nests in only one position on humeral bone 26. In this regard, humeral cut guide member 602 includes bone-engagement member 604 having bone-engagement surface 660 that is complementary and made to substantially mate and nest in only one position (i.e., as a substantially negative or mirror or inverse surface) with a three-dimensional bone surface of humeral bone 26 with or without associated soft tissues, which is reconstructed as a 3-D image via the aforementioned CAD or software. Humeral cut guide member 602 also includes registration member 614 having surfaces 662 and 664 that are patient-specifically sized and shaped to mate with bicipital groove 78 (FIG. 6) of humeral bone 26.

Registration member 614 is an elongated tab-shaped member having proximal end 618 unitary with or connected to bone-engagement member 604, and distal end 616 located away from bone-engagement member 604. With primary member 608, supports 612 and 613, and elongated registration member 614, humeral cut guide member 602 is configured to nest with humeral head 26 in a single position with as little material as possible. In this manner, a majority of humeral head 26 is exposed during the surgical procedure to allow the surgeon greater visual access to the humeral bone 26. Furthermore, humeral cut guide member 602 is flexible so as to be able to bend into position on humeral bone 26 with surgeon assistance through use of protrusions 620A and 620B.

In the example of humeral cut guide member 602, distal end 616 includes protrusion 620A and support 622 that further provide registration with humeral head 26 via patient-specific surface 666. In particular, support 622 extends the width of registration portion 616 to increase the patient-specific fit with humeral bone 26. Protrusion 620A also includes curved contact surface 668 that allows registration member 614 to be manipulated by the surgeon into correct alignment on humeral bone 26. Sidewalls 670A and 670B connect to and diverge away from the pair of supports 612A and 612B, respectively, and are joined by contact surface 668. Registration member 614 may also include protrusion 620B that provides curved contact surface 672 that allows humeral cut guide member 604 to be manipulated by the surgeon into correct alignment on the humeral bone 26. The surgeon may place a finger-tip upon contact surface 672 and a thumb on contact surface 668, which allows the surgeon to squeeze registration member 614 to orient the humeral cut guide member 604 and ensure that bone-engagement surfaces 660, 662, 664 and 666 properly align with bone surfaces of humeral bone 26. Cut guide member 602 can be made of flexible material, such as polymers, to allow registration member 614 and bone-engagement member 604 to flex to accommodate slight imperfections in patient-specific surfaces 660-666 or misalignments in registration member 614 and bone-engagement member 604. Thus, a surgeon can press down on protrusions 620A and 620B to force patient-specific surfaces 660-666 into position, which may cause slight bending of registration member 614 and bone-engagement member 604 in the process.

As best illustrated in FIG. 21A, bone-engagement member 604 includes an elongated primary member 608 extending in a first direction (i.e., a direction parallel with a coronal plane of the body) over humeral bone 26, including pin guide aperture 610. Pin guide aperture 610 is aligned per the specific patient and allows for passage of a drill, Steinmann pin, or guide wire (not shown), that allows humeral bone 26 to be prepared, (e.g., reamed) at the appropriate location for any desired resurfacing of humeral bone 26. Bone-engagement member 604 also includes a pair of supports 612A and 612B and a pair of supports 613A and 613B extending substantially orthogonal to primary member 608. Supports 612 and 613 define portions of bone-engagement surface 660, and assist in mating and nesting humeral cut guide member 602 in only one position on humeral bone 26 with or without associated soft tissues.

Humeral cut guide member 602 includes cut guide plate 624 including elongated slot 626. Cut guide plate 624 is connected to registration member 614 with a tube shaped, elongate member 628 that extends outward from registration member 614 such that cut guide plate 624 may be spaced apart from humeral bone 26. By spacing cut guide plate 624 away from humeral bone 26, the unnecessary removal of soft-tissue (e.g., muscle, cartilage, etc.) from humeral bone 26 is prevented, which assists in the patient's recovery after the arthroplasty. Although elongate member 628 extends outward from registration member 614 to an extent that cut guide plate 624 will be spaced apart from humeral head 26, it should be understood, however, that the location of cut guide plate 624 may be adjusted along elongate member 628 such that cut guide plate 624 may be moved closer to humeral bone 26, if desired.

More specifically, cut guide plate 624 includes a connection portion 630 at end 632 thereof that is configured to mate with elongate member 628. Further, connection portion 630 may include mating socket 634 that is designed to allow elongate member 628 to smoothly slide therein. In this regard, connection portion 630 may be urged along elongate member 628 to adjust the position of cut guide plate 624 relative to humeral bone 26 in an infinite number of positions. As connection portion 630 is urged along elongate member 628, the T-shape of elongate member 628 slides within the corresponding T-shape of socket 634. Connection portion 630 may then be moved when a force sufficient to overcome the friction between socket 634 and elongate member 628 is applied. Once the force is removed, the frictional engagement between the T-shaped members holds cut guide plate 624 in the desired location without the aid of protrusions 536 and aperture 534 (FIG. 14). In this manner, the position of cut guide plate 624 may be selectively adjusted based on the preferences of the surgeon during the shoulder arthroplasty. Connection portion 630 can include flange 674 that can be grasped by a surgeon to facilitate movement of cut guide plate 624 on elongate member 628. It should be understood that although cut guide plate 624 has been described above as being movable along elongate member 628, the present disclosure contemplates configurations where cut guide plate 624 is immovably fixed to elongate member 628.

As best shown in FIG. 21A, cut guide plate 624 includes upper member 638 spaced apart from lower member 640, with elongated slot 626 defined by gap 642 between upper member 638 and lower member 640. Lower member 640 defines elongated apertures 644A and 644B that are configured to receive a drill (not shown) for drilling humeral bone 26. After drilling of the humeral bone 26, a pin (not shown) such as a Steinmann pin or K-wire may be implanted in humeral bone 26, which may be used to assist in positioning humeral cut guide member 602 relative to humeral bone 26. In the illustrated embodiment, elongated apertures 644A and 644B travel parallel to elongate member 628 to allow cut guide plate 624 to move along elongate member 628 without interference from the pin (not shown). If cut guide plate 624 is immovably fixed to elongate member 628, however, it will be appreciated that elongated apertures 644A and 644B may extend in a non-parallel manner relative to elongate member 628 to assist in securing cut guide member 602 to humeral bone 26. Although a pair of elongated apertures 644A and 644B are illustrated in the figures, it should be understood that more or fewer elongated aperture may be used.

Although not required, lower member 640 may define a surface, such as surface 546 of FIG. 14, that extends outward relative to upper member 638 such that a shelf or platform is formed. The platform allows for a greater amount of surface area for the tool blade (not shown) to lie upon during resurfacing or resecting of humeral bone 26. In this manner, the tool blade is substantially prevented from being improperly angled during the resurfacing or resecting of humeral bone 26 to form a planar surface.

As shown in FIG. 21A, support bar 650 may fix upper member 638 to lower member 640. Support bar 650 is formed at an opposite end 652 of cut guide plate 624 relative to end 632 of elongate member 628. Support bar 650 assists in maintaining the proper gap 642 between upper member 638 and lower member 640. Notwithstanding, it should be understood that support bar 650 is removable during surgery by cutting support bar 650 with the saw or blade for resecting or resurfacing humeral bone 26, as desired by the surgeon. It should be understood that although elongate member 628 is illustrated as fixing cut guide plate 624 in an infinite number of positions relative to humeral head 26, tube-shaped member 628 may be adjustable as illustrated in FIGS. 14-19 into a plurality of discrete positions.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

VARIOUS NOTES & EXAMPLES

Example 1 can include or use subject matter such as a humeral cut guide system for a humeral head, the humeral cut guide system comprising: a bone-engagement member including a first patient-specific bone-engagement surface that is complementary and made to substantially mate and nest in only one position on a specific patient's humeral head; a registration member connected to the bone-engagement member including a second patient-specific bone engagement surface that is sized and made to substantially mate and nest in only one position with the specific patient's bicipital groove; a first protrusion extending from the registration member and having a first surgeon-engaging surface for manipulation by a surgeon; and a cut guide plate connected to and extending away from the registration member such that, upon the bone-engagement member mating and nesting with the specific patient's humeral head, the cut guide plate is spaced apart from the humeral head, wherein the cut guide plate defines an elongate slot.

In Example 2, the subject matter of Example 1 can optionally include a second protrusion extending from a junction between the bone-engagement member and the registration member.

In Example 3, the subject matter of Example 2 can optionally include a second protrusion including: a pair of supports extending from respective sides of the registration portion; a pair of sidewalls connected to and diverging away from the pair of supports; and a second surgeon-engaging surface connecting the pair of sidewalls to each other.

In Example 4, the subject matter of any one or more of Examples 2-3 can optionally include a registration member that is flexible between the first and second protrusions.

In Example 5, the subject matter of Example 4 can optionally include a bone-engagement member and a registration member that are comprised of a polymer material.

In Example 6, the subject matter of any one or more of Examples 4-5 can optionally include a registration member including a first portion and a second portion, the first portion having the second patient-specific bone engagement surface and the second portion having a third patient-specific bone engagement surface that is sized and made to substantially mate and nest in only one position with the specific patient.

In Example 7, the subject matter of any one or more of Examples 1-6 can optionally include a first protrusion including a registration flange extending from a juncture of the registration member and the first protrusion.

In Example 8, the subject matter of Example 7 can optionally include a registration flange comprising a curved body having an inner surface for contacting bone and an outer surface for engaging a thumb of a surgeon.

In Example 9, the subject matter of Example 8 can optionally include an inner surface that is shaped to mate on a lateral surface of a humeral bone opposite a humeral head.

In Example 10, the subject matter of any one or more of Examples 8-9 can optionally include an inner surface that is patient-specific and an outer surface that includes a concave contour.

In Example 11, the subject matter of any one or more of Examples 1-10 can optionally include: an elongate member extending from the registration member; and a connection portion connected to the cut guide plate; wherein the elongate member is configured to smoothly slide along the connection portion.

In Example 12, the subject matter of Example 11 can optionally include an elongate member that is infinitely positionable along the connection portion.

In Example 13, the subject matter of any one or more of Examples 11-12 cab optionally include an elongate member that has a T-shape and a connection portion that has a corresponding T-shaped socket.

Example 14 can include or use subject matter such as a humeral cut guide system for a humeral head, comprising: a bone-engagement member including a first patient-specific bone-engagement surface that is complementary and made to substantially mate and nest in only one position on a specific patient's humeral head; a registration member connected to the bone-engagement member including a second patient-specific bone engagement surface that is sized and made to substantially mate and nest in only one position with the specific patient's bicipital groove; an elongate member extending from the registration member; and a cut guide plate having a connection portion with a socket configured to receive the elongate member such that a position of the cut guide plate relative to the specific patient's humeral head is selectively adjustable along the elongate member in an infinite number of positions.

In Example 15, the subject matter of Example 14 can optionally include an elongate member that is configured to smoothly slide along the socket of the connection portion.

In Example 16, the subject matter of any one or more of Examples 14-15 can optionally include an elongate member that has a T-shape and a slot of the connection portion that has a corresponding T-shaped socket.

Example 17 can include or use subject matter such as a method of resecting or resurfacing a humeral head using a humeral cut guide, the method comprising: positioning a bone-engagement member along a humeral head surface of a humeral bone; positioning a registration member along a bicipital groove surface of a humeral bone; squeezing the registration member and the bone-engagement member to ensure seating of the humeral cut guide; sliding a cut guide plate along an elongate member extending from the humeral cut guide to engage the humeral head surface of the humeral bone; and resecting or resurfacing the humeral head using a cutting device engaged with the cut guide plate.

In Example 18, the subject matter of Example 17 can optionally include manipulating the humeral cut guide using a pair of protrusions extending from opposite ends of the registration member.

In Example 19, the subject matter of Example 18 can optionally include a bone-engagement member and a registration member that include first and second patient-specific surfaces, respectively.

In Example 20, the subject matter of any one or more of Examples 17-19 can optionally include smoothly sliding the cut guide plate along the elongate member through an infinitely small number of positions to reach a resecting or resurfacing position.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of resecting or resurfacing a humeral head using a humeral cut guide, the method comprising:
    positioning a bone-engagement member along a humeral head surface of a humeral bone;
    positioning a registration member along a bicipital groove surface of a humeral bone;
    squeezing the registration member and the bone-engagement member to cause bending of the registration member relative to the bone-engagement member and thereby ensure seating of the humeral cut guide;
    sliding a cut guide plate along an elongate member extending from the humeral cut guide to engage the humeral head surface of the humeral bone; and
    resecting or resurfacing the humeral head using a cutting device engaged with the cut guide plate.

2. The method of claim 1, further comprising manipulating the humeral cut guide using first and second protrusions extending from opposite ends of the registration member, wherein the first protrusion and the second protrusion are concavely contoured to engage a finger of a user of the humeral cut guide system.

3. The method of claim 2, wherein the bone-engagement member and the registration member include first and second patient-specific surfaces, respectively.

4. The method of claim 1, further comprising smoothly sliding the cut guide plate along the elongate member to reach a resecting or resurfacing position.

5. The method of claim 1, wherein resecting or resurfacing the humeral head using the cutting device engaged with the cut guide plate comprises sliding a cutting blade of the cutting device along a platform extending from the cut guide plate.

6. The method of claim 1, wherein the bone-engagement member comprises an elongated primary member and a pair of secondary members extending substantially orthogonaly to the elongated primary member, further comprising positioning the pair of secondary members along the humeral head to stabilize the humeral cut guide.

7. The method of claim 1, further comprising:
    positioning a pin guide aperture in the bone-engagement member such that a first pin is configured to be guided through the pin guide aperture to extend into the humeral head; and
    positioning an aperture in the cut guide plate such that a second pin is configured to be guided through the aperture to extend into the humeral head, the aperture extending along an axis parallel to the elongate member.

8. The method of claim 1, wherein resecting or resurfacing the humeral head using the cutting device engaged with the cut guide plate comprises cutting through a support bar coupling an upper member and a lower member forming an elongate slot in the cut guide plate.

9. The method of claim 1, wherein the humeral cut guide is fabricated from a polymeric material to facilitate bending.

10. The method of claim 1, wherein:
    the humeral cut guide continuously engages the humeral bone along a path comprising the bone-engagement member, an interface between the bone-engagement member and the registration member and the registration member; and
    squeezing of the registration member and the bone-engagement member ensures seating of the humeral cut guide along the path.

11. The method of claim 10, further comprising manipulating the humeral cut guide using a first protrusion and a second protrusion extending from the registration member.

12. A method of resecting or resurfacing a humeral head using a humeral cut guide member including a bone-engagement member that includes a first patient-specific bone-engagement surface that is complementary and made to substantially mate and nest in only one position on a specific patient's humeral head, and including a cut guide plate connected to the bone-engagement member, the method comprising:

affixing the humeral cut guide member to the only one position of the specific patient's humeral head;

selectively adjusting a position of the cut guide plate relative to the specific patient's humeral head by moving the cut guide plate along an elongate member;

orienting a proximal end of a registration member connected to the humeral cut guide member into the specific patient's bicipital groove, the registration member being connected to the humeral cut guide member and including a second patient-specific bone engagement surface that is sized and made to substantially mate and nest in only one position with the specific patient's bicipital groove;

wherein:

the proximal end of the registration member is connected to a first end of the bone-engagement member and to the elongate member; and a distal end of the registration member extends from the proximal end and is connected to a first protrusion; and manipulating the humeral cut guide member using the first protrusion and a second protrusion extending from the proximal end of the registration member proximate the bone-engagement member.

13. The method of claim 12, further comprising engaging a support extending from the first protrusion across a portion of a surface of a humeral bone of the humeral head.

14. The method of claim 12, further comprising smoothly sliding the cut guide plate along the elongate member to reach a resecting or resurfacing position.

15. The method of claim 14, wherein the elongate member has a T-shape and the cut guide plate includes a connection portion having a corresponding T-shaped socket.

16. The method of claim 12, further comprising incrementally sliding the cut guide plate along the elongate member through engagement of an aperture with protrusions to reach a resecting or resurfacing position.

17. The method of claim 12, wherein the registration member is unitary with the bone-engagement member.

\* \* \* \* \*